United States Patent
Ray et al.

(10) Patent No.: US 12,310,696 B2
(45) Date of Patent: May 27, 2025

(54) NON-INTRUSIVE MONITORING SYSTEM

(71) Applicant: Nomo International, Inc., Edina, MN (US)

(72) Inventors: Kevin Ray, Oakland, CA (US); Cristian Codreanu, Chicago, IL (US); Kris Winer, Danville, CA (US)

(73) Assignee: NOMO INTERNATIONAL, INC., Edina, MN (US)

( * ) Notice: Subject to any disclaimer, the term of this patent is extended or adjusted under 35 U.S.C. 154(b) by 161 days.

(21) Appl. No.: 18/172,610

(22) Filed: Feb. 22, 2023

(65) Prior Publication Data

US 2023/0263393 A1    Aug. 24, 2023

Related U.S. Application Data

(60) Provisional application No. 63/268,329, filed on Feb. 22, 2022.

(51) Int. Cl.
    *A61B 5/00*           (2006.01)
    *A61B 5/11*           (2006.01)

(52) U.S. Cl.
    CPC .......... *A61B 5/0022* (2013.01); *A61B 5/0077* (2013.01); *A61B 5/1112* (2013.01)

(58) Field of Classification Search
None
See application file for complete search history.

(56) References Cited

U.S. PATENT DOCUMENTS

| | | | |
|---|---|---|---|
| 2007/0156450 A1* | 7/2007 | Roehm | G16H 40/67 600/300 |
| 2012/0233679 A1* | 9/2012 | Shedrinsky | A61B 5/002 726/7 |
| 2017/0272842 A1* | 9/2017 | Touma | A63B 24/0003 |
| 2021/0057093 A1* | 2/2021 | deSa | G08B 21/0423 |
| 2021/0174954 A1* | 6/2021 | Truschel | A61B 5/1118 |
| 2021/0311166 A1 | 10/2021 | Wu et al. | |
| 2023/0302206 A1* | 9/2023 | Usman | G16H 40/67 |

OTHER PUBLICATIONS

International Search Report and Written Opinion mailed Nov. 2, 2023 for International Patent Application No. PCT/US23/63008.

* cited by examiner

*Primary Examiner* — Thomas S McCormack
(74) *Attorney, Agent, or Firm* — Perkins Coie LLP

(57) ABSTRACT

Methods, devices and monitoring systems are described that include a hub in communication with sensors that aggregate activities in an enclosure, such as a building. The hub identifies when those activities are occurring more or less often than expected and classifies the activity to piece together and learn the user's or individual's daily activity. Additional satellite devices may be added that increase the range and capacity of the sensors for collecting more information and activity within the building. In this manner, the monitoring systems use a redundant array of sensors to consistently monitor activities occurring in or around a building to create a trail and heatmap of events and activities that the monitoring system's hub classifies, verifies with other sensors, learns, and then correctly processes.

28 Claims, 7 Drawing Sheets

NON-INTRUSIVE MONITORING SYSTEM

CROSS-REFERENCE TO RELATED APPLICATIONS

This application claims priority to U.S. Provisional Application No. 63/268,329 titled "NON-INTRUSIVE MONITORING SYSTEM" filed on Feb. 22, 2022, the contents of which are incorporated herein by reference in their entirety.

TECHNICAL FIELD

The present disclosure relates to monitoring devices, and more particularly relates to a non-intrusive monitoring system.

BACKGROUND

Conventional monitoring systems require considerable user intervention and interaction to be reliably setup to monitor human activity in a building and provide a corresponding response for the human activity. However, after being setup to monitor human activity, the process of monitoring human activity in conventional monitoring systems is still prone to false positives and conventional monitoring systems require training and additional information. Therefore, there is a need for improved monitoring systems that can be implemented with lower cost while providing reliable monitoring capabilities.

Figure 1:
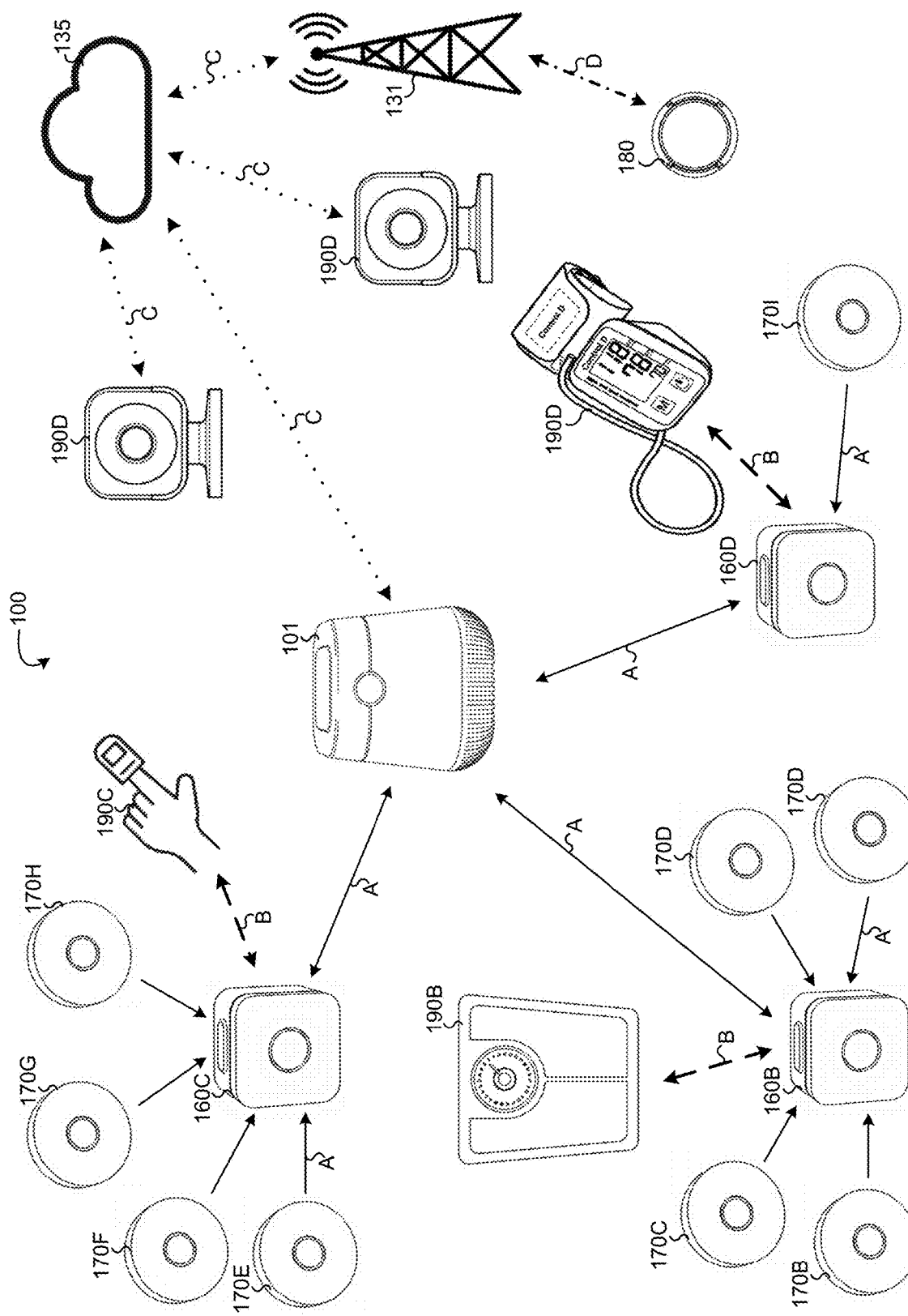
FIG. 1 illustrates an exemplary network environment for implementing the exemplary monitoring system in accordance with an exemplary embodiment of the present disclosure.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the scope of the disclosure as defined by the appended claims.

DETAILED DESCRIPTION

In this patent document, the term "exemplary" is used to describe an example or a particular embodiment of the disclosed devices, components systems and/or methods. Specific details of several embodiments of monitoring systems and associated systems and methods are described below.

In this disclosure, numerous specific details are discussed to provide a thorough and enabling description for embodiments of the present disclosure. One of ordinary skill in the art will recognize that the disclosure can be practiced without one or more of the specific details. Well-known structures and/or operations often associated with monitoring devices and monitoring systems may not be shown and/or may not be described in detail to avoid obscuring other aspects of the disclosure. In general, it should be understood that various other devices, systems, and/or methods in addition to those specific embodiments disclosed herein may be within the scope of the present disclosure.

The term "monitoring system" can refer to an assembly of one or more electronic devices, smart devices, cameras, sensors, radio transmitters and receivers. The term "monitoring system" can generally refer to a device coupled to one or more sensors that measure a physical quantity and converts the measured quantity into a signal. The monitoring system may be a single monitoring device that collects or measures one or more physical quantities. The monitoring system may exclude an image sensor to allow for non-intrusive or non-visual data collection or data collection outside of the visible spectrum. The monitoring system may include a low-resolution image sensor or high-resolution image sensor configured to selectively collect visual data in a non-intrusive manner. A monitoring device can include, for example, one or more sensors, electronic circuitry, and one or more communication modules.

Conventional home monitoring systems use one or more smart home devices (e.g., cameras, lights, thermostats, locks, etc.,) and smart device accessories (e.g., motion sensors, environmental sensors, and trigger sensors) combined with pre-programmed sounds and detected events to detect and monitor human and pet activity, smoke, fire, air quality and humidity, and to listen for specific sounds such as baby crying or glass breaking. Although, conventional home monitoring systems may be used to monitor all activity in a household and filter through specific activity before notifying a user, for home monitoring systems to be practical and effective, users are often required to network multiple cameras with smart home devices and/or sensors to determine what occurred in the home and are then asked to manual enter a corresponding task, collect data, analyze, and report the activity data to the user. The process of determining an activity and corresponding response is a complicated process and a hassle for typical users. Moreover, user intervention and device training is often required to prevent false positives, for example, filtering out a break-in or suspicious activity alert from events such as drapes blowing or pets moving around the house. To prevent false positives, conventional home monitoring system then need to be trained or setup to monitor for a specific family setup or floorplan by knowing/monitoring the activity of every family member and pet in a household. For example, monitoring for glass break or a break-in, requires a home monitoring system to constantly monitor and know (preferably multiple) user locations, phone locations, personal information, and sensed motion information (preferably audio and/or visual recognition) from all potential entry points to always ensure the safety of family members.

Further, more accurate and costly conventional monitoring systems use sophisticated integration of devices and/or costly hardware that collect, store, retrieve, and compare user's profile, voice, face, or image recognition data that is vulnerable to security hacks, can lead to identity theft, and still requires considerable training and setup to work reliably. Thus, proper setup of monitoring systems to account for pets, drapes blowing, and random human activity and behavior can be very costly, complicated and a hassle for typical users. Further, to be practical and effective in monitoring users and providing peace of mind, monitoring systems require comprehensive surveillance of multiple spaces within a building to account for user variability and human activity, which is often intrusive or costly, puts users at risk to security hacks or identity theft, and/or poses a privacy concern for users who want peace of mind but do not want to their personal information and whereabout collected, stored, and shared.

The conventional monitoring systems may also produce measurements, alerts and, more generally, excess data points that may do convey useful information unless properly aggregated, analyzed and/or interpreted. Embodiments of the present disclosure solve these challenges, and others, by providing a monitoring system hub in communication with simple and redundant sensors that aggregate activities in an enclosure, such as a building, that are sent to the hub. In some embodiments, the hub then identifies when those activities are occurring more or less often than expected and classifies the activity to piece together and learn the user's or individual's daily activity. Additional satellite devices may be added to the monitoring system hub that increase the range and capacity of sensors for collecting more information and activity within the building. In this manner, the monitoring system of the present disclosure uses a redundant array of sensors to consistently monitor activities occurring in or around a building to create a trail and heatmap of events and activities that the monitoring system hub classifies, verifies with other sensors, learns, and then correctly processes.

The monitoring system provides simple and redundant sensors to aggregate activities occurring in and around an enclosure, such as a building or structure, which are used to generate useful and relevant information that can be readily understood by the appropriate user(s). For example, in a home care scenario, where an elderly person is being monitored for a number of activities, the monitoring system can determine when those activities occur more or less often than expected, and to increase the ease of communicating briefly and succinctly with multiple caregivers when such activities occur or don't occur. The monitoring system of the present disclosure includes one or more components, including hub devices, satellite devices, and sensor devices for collecting visual or strictly nonvisual information, including but not limited to environmental measurements such as temperature, humidity, airflow, etc., measurements conducted by medical instrumentation, such as blood pressure measurements, body temperature measurements, as well as other measurements related to the well-being and the mobility of the building occupant(s).

The hub device may collect nonvisual information locally in the room in which it is installed. To collect information from other rooms with different events or features, the hub device may pair with one or more satellite devices which may act as Wi-Fi extenders for one or more hub devices. The satellite devices may communicate information collected from sensor devices installed throughout the building. The satellite devices may further pair with and collect information from other compatible electronic devices, for example, a bathroom scale or a blood pressure monitoring device. The monitoring system may use proprietary Wi-Fi communication protocol "ESPNow" from Espressif chip manufacturer. One or more components of the monitoring device may include activity or event classifiers to learn and determine an individual's daily activities (e.g., walking, meal prep, or toileting) that are used together with one or more sensors to corroborate what happened and confirm what was learned.

FIG. 1 illustrates an exemplary network environment for implementing the exemplary monitoring system in accordance with an exemplary embodiment of the present disclosure. As can be seen with reference to FIG. 1, an exemplary network environment 100 for implementing a monitoring system comprises various sensors and devices communicably coupled together in accordance with one or more embodiments of the present disclosure. Not all of the depicted components may be required. However, one or more implementations may require additional components, fewer components or different components not shown in network environment 100. Thus, any variations in network environment 100 may be implemented without departing from the scope of the present disclosure.

Network environment 100 may be include one or more networks such as an IoT network, a WiFi network, a Bluetooth network, a private network, the internet, any other network, or combinations thereof. The network environment 100 includes one or more satellite devices 160A, 160B, 160C . . . etc., (hereinafter referred to as 160). One or more of the satellite devices 160, such as satellite device 160C, may be configured to communicate (e.g., via wired or wireless communication) with one or more satellite devices 160B, one or more sensor devices 170B, and/or one or more hub devices 101. The network environment 100 includes one or more sensor devices 170A, 170B, 170C, 170D, 170E, 170F, 170G, 170H, 170I . . . etc., (hereinafter referred to as 170). One or more of the sensor devices 170, such as sensor device 170H, may be configured to communicate (e.g., via wired or wireless communication) with one or more satellite devices 160B and/or one or more hub devices 101. The network environment 100 includes one or more electronic devices 190A, 190B, 190C, 190D . . . etc., (hereinafter referred to as 190). One or more of the electronic devices 190, such as electronic device 190A, may be configured to communicate (e.g., via wired or wireless communication) with one or more satellite devices 160B and/or one or more hub devices 101. The network environment 100 includes one or more hub devices 101 in communication with one or more satellite devices 160 and one or more electronic device 190. Each hub device 101 may communicably couple to one or more servers within a cloud infrastructure 135.

In some embodiments, the electronic devices 190 may include, may be embedded in, or may be coupled to a portable communication device, such as a mobile phone, a laptop, a wearable device, a tablet or any other communication device. The electronic devices 190 may be communicably coupled to one or more of the satellite devices 160, and/or to one or more other devices of the electronic devices 190. As depicted in FIG. 1 examples of electronic devices 190 may include a scale, a finger oximeter, a blood pressure monitoring device, a spirometer, a wearable device (e.g., watch, band, belt, etc.,), a thermometer, an oxygen machine or mask (e.g., a nasal cannula oxygen machine), a camera, a computer, a desktop, a laptop, a tablet, a fax machine, a printer, light bulb, an appliance, and so forth.

In some embodiments, satellite devices 160 facilitate wireless communication between one or more hub devices 101, and one or more electronic devices 190 and sensor devices 170, and one or more servers within a cloud infrastructure 135. In some embodiments, satellite devices 160 may be on the same local area network as hub device 101. In some embodiments, satellite devices 160 may be configured to form a new local area network communicably coupled to hub device 101. The satellite devices 160 may communicatively couple one or more electronic devices 190 to one or more sensor devices 170, and vice versa. In one or more implementations, one or more of satellite devices 160 may be referred to as an IoT network and/or a machine-to-machine (M2M) network.

One or more of the sensor devices 170 may be referred to as an IoT device and/or an M2M device and may include human-machine interface (HMI) applications and machine-interface applications. The sensor devices 170 in some embodiments can be implemented as tags that can be attached to or carried by a person, or can be mounted on a wall or another surface. There may be multiple paths between one or more of the sensor devices 170 and/or one or more of the satellites 160. One or more of the satellites 160 and/or sensor devices 170 may be configured to communicate with one another or other systems and with one or more hub devices 101. One or more of the sensor devices 170 may include or may be a sensor that measures a physical quantity from surrounding environment and convert physical quantities into a signal. Examples of sensors include, by way of illustration only and not by way of limitation, temperature sensors, video cameras, audio recorders, motion sensors, humidity sensors, smoke detectors and other sensors. In some embodiments, the sensor devices 170 may all measure the same physical quantity from surrounding environment and convert physical quantities into a signal to provide redundancy/verify the measure physical quantity, for example, the sensor devices 170 may all measure motion and/or sound to confirm motion or sound occurred in a space.

One or more of the electronic devices 190 may be referred to as an IoT device and/or an M2M device and may include human-machine interface (HMI) applications and machine-interface applications. There may be multiple paths between one or more of the electronic devices 190 and/or one or more of the satellites 160. One or more of the satellites 160 and/or electronic devices 190 may be configured to communicate with one another or other systems and with one or more hub devices 101. One or more of the electronic devices 190 may include or may be a sensor that measures a physical quantity from surrounding environment and convert physical quantities into a signal. Examples of sensors include, by way of illustration only and not by way of limitation, temperature sensors, video cameras, audio recorders, motion sensors, humidity sensors, smoke detectors and other sensors. In some embodiments, the electronic devices 190 may all measure a similar physical quantity from surrounding environment and convert physical quantities into a signal to provide redundancy/verify the measure physical quantity, for example, the electronic devices 190 may all measure motion and/or sound to confirm motion or sound occurred in a space.

In one or more embodiments, electronic devices 190 may include one or more of active devices, passive devices and/or implemented wholly or partially as system on chip devices. Electronic devices 190 may include a transmitter, a receiver, a Global Positioning System (GPS), a Bluetooth (BT)/BLE transceiver and/or a WiFi™ transceiver. Similarly, sensor devices 170 may include one or more of active devices, passive devices and/or implemented wholly or partially as system on chip devices. Sensor devices 170 may include a transmitter, a receiver, a Global Positioning System (GPS), a Bluetooth (BT)/BLE transceiver and/or a WiFi™ transceiver. In one or more embodiments, satellite devices 160 may include and provide one or more network access points, such as a wireless access point (WAP), communicably coupling electronic devices 190 and/or sensor devices to one or more hub devices 101.

Various communication protocols A, B, C, and D may be used within network environment 100 for device provisioning and/or communication. Provisioning between hub devices 101, satellite devices 160 and sensor devices 170 may use proprietary Wi-Fi communication "A" and out of band signaling. Communication "A" may include proprietary Wi-Fi communication protocol "ESPNow" from Espressif chip manufacturer. The ESPNow protocol may be used to directly broadcast new device (e.g., satellite device 160 or sensor device 170) provisioning information directly to the hub device 101. The hub device 101 may then build a whitelist of known sensors and devices in and around the building and request wireless user through a human-machine-interface (HMI) (e.g., an App) to manual add devices or sensors not on the whitelist, the MAC address of the gateway for pairing device may be then sent directly to the new device or sensor.

Communication "B" (e.g., Bluetooth (BT)/Bluetooth Low Energy (BLE)) may be used as the communication protocol of electronic devices 190 with satellite device 160. Communication "C" (e.g., IEEE 802 standard) may be used as the communication protocol of hub device 101 with cloud infrastructure 135, local antenna 131 with cloud infrastructure 135, and IoT/camera devices 190D with cloud infrastructure 135. Communication "D" (e.g., broadband cellular network, e.g., 2G/3G/4G/5G, or wireless broadband communication, e.g., Long-Term Evolution (LTE)) may be used as the communication protocol between pendant 180 with cloud infrastructure 135.

All detected or user inputted environmental information (e.g., temperature, humidity, sounds, pressure, air flow, air quality, pets, location of windows and doors, ambient light, outside weather, etc.,) and individual information (age, posture, mobility, gait, height, weight, vitals, medication, physical address, medical conditions, physical activity requirements, etc.,) may be classified in the hub device 101. The aggregated environmental and/or individual information (hereinafter "activity information") is collected by the hub device 101 from sensor devices 170 and electronic devices 190, either directly from the hub device 101 or through one or more satellite devices 160. The collected activity information is then used by the hub device 101 to build a map of what happened, where it happened, and what sensors are involved. The hub device 101 then classifies each activity information from various sensor devices 170 and electronic devices 190 to determine the occurrence or non-occurrence of an event. For example, a caregiver may wish to monitor and ensure an individual with a medical condition (e.g., liver cirrhosis) is having adequate physical activity and urination/bowel movements. The hub device 101 may receive individual information from a caregiver/user input/remote computing device (e.g., the individual's medical condition, height, weight, vitals, etc.,) and a request to monitor the individual for certain activities for managing or improving the medical condition. The caregiver may place electronic devices 190 and/or sensor devices 170 within a proximity of the hub device 101 to monitor the individual's progress. As an example, the individual may get out of bed to go to the bathroom, in doing so, sensor devices 170 and electronic devices 190 may detect the individual's motion and trajectory into the bathroom and subsequently detect only the sound of a faucet having occurred while the individual made a bathroom visit. The hub device 101 collects the activity information from sensor devices 170 and electronic devices 190 and may make multiple classifications, a first classification includes physical activity (e.g., a walking event) followed by turn of the faucet handle (e.g., arm movement/motion). However, additional activity information (subsequent activity) from sensor devices within or near the bathroom confirms that the shower or toilet was not used. Thus, a second classification is made that a non-occurrence of a bowel movement happened. The hub device 101 may continue to monitor the individual for the second classification, and if, the classification does not occur the hub device 101 may contact/inform a caregiver and/or remind the individual to either take medication to stimulate a bowel movement, perform additional walking events, or take meals or drinks to help with digestion, or any combination thereof. The hub device 101 may report the activities in textual format to the caregiver as a daily digest or journal of occurred and non-occurred individual events.

One or more sensor devices 170 and electronic devices 190 may further collect additional information, for example, the individual entering or leaving a room, standing, sitting, falling, various sound effects, sounds or movement of pets or animals. The sensor devices 170 and electronic devices 190 may store locally in a database or access remotely stored acoustic and/or video signatures used to indicate one or more events/activities occurring. In some embodiments, the hub device 101 may store locally in a database or access remotely stored acoustic and/or video signatures and compare/classify the activity with stored acoustic and/or video signatures. Artificial intelligence (AI) or machine learning (ML) may be used to together with Time-of-Flight (ToF) sensors, acoustic and/or video signatures to determine when an individual is feeling discomfort or in trouble. For example, Time-of-Flight (ToF) sensors and sound and/or video signatures paired with AI/ML may be used to determine whether collected activity information from various sensor devices 170 and electronic devices 190 are indicative of an individual being susceptible to falling. In such instances, the monitoring device may be used to provide caregivers with fall detection based on, for example, the individuals posture or movement information into/out of/towards a chair or bed. The caregiver may add additional sensor devices 170 and electronic device 190 to monitor activity in other rooms or the individual's vitals. The hub device 101 may then use collected activity information from individual sensors and devices to build the individuals habits, preferences, and progress in treating or managing the medical condition. The hub device 101 may be configured to collect only non-visual information from activity information may to protect the individual's privacy. The collected activity information may then be sent to caregivers by text message.

Figure 2:
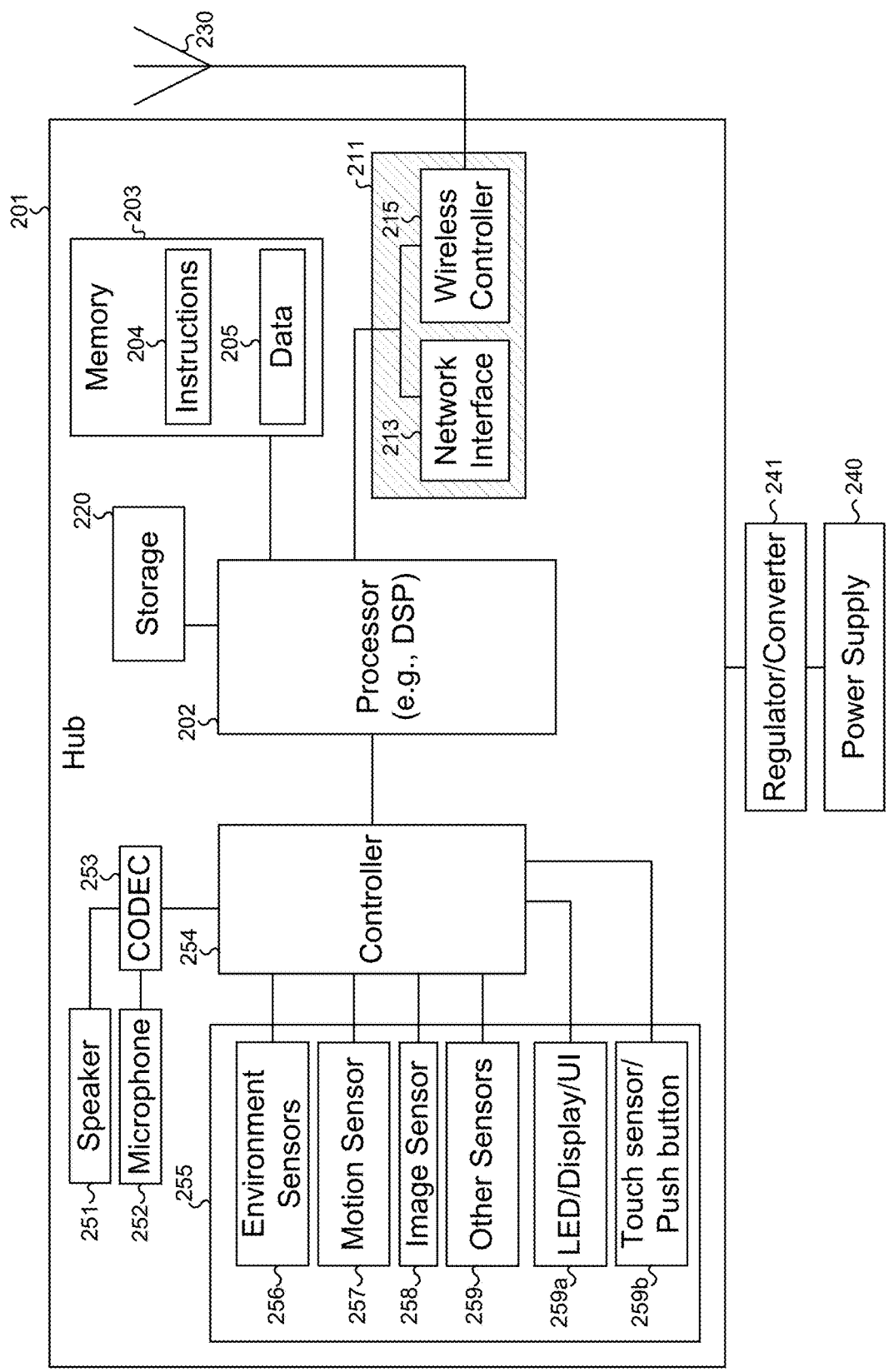
FIG. 2 illustrates conceptually an exemplary hub device of the monitoring system with which some implementations of the present disclosure may be implemented.

FIG. 2 illustrates conceptually an exemplary hub device of the monitoring system with which some implementations of the present disclosure may be implemented. As can be seen with reference to FIG. 2, an exemplary hub device 201 may include one or more of the following: processor 202, memory 203 having instructions 204 and/or data 205, network module 211, network interface 213, wireless controller 215, additional/external storage 220, antennas 230, power supply 240, power regulator/convertor 241, speaker 251, microphone 252 (e.g., PDM microphone), CODEC 253, and controller 254. The hub device 201 may further include one or more sensor components 255 that includes at least one environmental sensor 256, motion sensor 257, and image sensors 258 (e.g., a CMOS sensor), other sensors 259 (e.g., a passive infrared (PIR) sensor, white light PIR sensor, etc.,), and at least one light emitting sources 259*a* (e.g., one LED, an array of LEDs, nightlight, etc.,), and one or more press features 259*b*. In some embodiments, one or more sensor components 255 may not be implemented as part of the hub device 201 but as separate components or sensors that can be in communication with the hub device 201. The hub device 201 may be any electronic device that transmits signals over a network, such as electronic devices embedded in smart appliances and other smart systems. The hub device 201 may include various types of computer readable media (e.g., a non-transitory computer-readable medium) and interfaces for various other types of computer readable media. The satellite device 360 and sensor device 470 may contain one, none, some, or all the components of the hub device 201 as described below and in the present disclosure.

The device hub 201 may use custom, public, or private graphical user interface for voice over IP and telephony (e.g., FreePBX), or Session Initiation Protocol (SIP), with Dual-Tone Multi-Frequency (DTMF) attachment to facilitate a virtual conference call. The hub device 201 may include custom, public, or private DSP to facilitate duplex audio. The hub device 201 may include Message Queuing Telemetry Transport Technical Committee (MQTT) for device-to-device messaging.

The processor 202 may retrieve and execute instructions 204 and/or data 205 from memory/storage 203 to perform the processes of the present disclosure. Processor 202 may be a single processor, a multi-core processor, or multiple processors in different implementations. Referring to FIGS. 2-6, instructions and data for operating hub device 201 may be stored on, transmitted from, or received by any computer-readable storage medium (e.g., memory 203, 403 or additional/external storage 320, 420 of satellite device 360 or sensor device 470, or memory/storage 512 of one or more servers 511) storing data (e.g., data 205) that is accessible to a processor (e.g., the processor of server 511) during modes of operation of the hub device 201. The hub device 201 may access and execute instructions and/or data stored on any remote computing device 531 (e.g., mobile device 532, laptop 533, or tablet 534). The data 205 may be a method instruction as depicted in FIG. 6. The method instructions are executable by processor 202. In some embodiments, one or more other hub devices 501, satellite devices 560, sensor device 570, servers 511, electronic devices 590, remote computing devices 531, or any combination thereof, may collect and measure a physical quantity and/or provide instructions for configuring and operating the hub device 201 and/or communicating between user(s) and other remote, local, and/or wireless electronic devices.

The memory/storage 203 may include a dynamic random-access memory (DRAM) and/or a read-only memory (ROM). Memory/storage 203 may provide a temporary location to store data 205 and instructions 204 retrieved and processed by processor 202. Memory/storage 203 may include a non-volatile read-and-write memory that stores data 205 and instructions 204, even when Wi-Fi/Internet is off, that may be retrieved and processed by processor 202. For example, memory/storage 203 may include magnetic, solid state and/or optical media, memory/storage 203 may be a single or multiple memory units as necessary. The memory/storage 203 stores all collected visual, audio, textual, voice, motion, heat, proximity, etc., information provided directly from one or more satellite devices 560, sensor devices 570, electronic devices 590, or servers 511, or indirectly through a wireless connection to another electronic device(s), sensor device(s) (e.g., a wearable device).

Instructions may be stored in memory 203 and/or additional/external storage 220 for machine learning, including pose estimation for recognizing people or pets and their body position, for example, sitting or lying down. The memory 203 and/or storage 220 may further include instructions for time-of-flight measurement by, for example, measuring the trajectory and duration of object occluding the image sensor 258 to determine pose estimation for recognizing people or pets and their body position.

Hub device 201 couples to a network through a network interface 213. In some embodiments, network interface 213 is a machine-interface. In this manner, the hub device 201 may be a part of a network of computers, a local area network (LAN), a wide area network (WAN), or an Intranet, or a network of networks, for example, the Internet. A wireless controller 215 may be coupled to the processor 202. The wireless controller 215 may be further coupled to an antenna 230. The network module 211 may be integrated as system-in-package or system-on-chip device and/or collectively defined as having the network interface 213 and wireless controller 215. Network interface 213 and wireless controller 215 integrated into the network module 211 and being coupled to an antenna 230. Any or all components of hub device 201 may be used in conjunction with the subject disclosure. The network interface 213 may include cellular interfaces, WiFi™ interfaces, Infrared interfaces RFID interfaces, ZigBee interfaces, Bluetooth interfaces, Ethernet interfaces, coaxial interfaces, optical interfaces, or generally any communication interface that may be used for device communication.

The hub device 201, satellite device 360, and/or sensor device 470 may use Narrow Band IoT (NB-IoT), Mobile IoT (MIoT), 3rd Generation Partnership Project (3GPP), enhanced Machine-Type Communication (eMTC), Extended Coverage GSM Internet of Things (EC-GSM-IoT) or other similar Low Power Wide Area Network (LPWAN) radio technology to enable a wide range of devices and services to be connected using cellular telecommunications bands.

The hub device 201 is powered through a power supply 240. The power supply 240 may include disposable and/or rechargeable batteries (e.g., 2800 mAh rechargeable Li-Polymer battery), existing electrical wiring, a power supply adapter, or any combination thereof. Disposable batteries or rechargeable batteries, for example, nickel cadmium (NiCd), lithium (Li), AA, AAA, and/or rechargeable capacitors, for example, supercapacitors (SC) or ultracapacitors. The power supply 240 may supply power to hub device 201 by, for example, a power adapter for connecting to an outlet, a solar panels/cell, or any other renewable/alternative power supply source. The hub device 201 may use multiple battery types, multiple power sources, etc., for example, using a coin cell battery to operate some sensor components 255 or to provide auxiliary power to power and operate one or more emergency electronic devices 590 during brown outs, black outs, or other power outages. Moreover, a converter/regulator 241; transformer or voltage regulator, AC to DC or DC to DC power converter, or frequency converter may be used separately (electrically coupled to the hub device 201) or integrated within the hub device 201 to provide adequate input power to the hub device 201 (e.g., 12 VDC).

The hub device 201 may include a speaker 251 and microphone 252 for communicating with an individual or receiving control commands from an individual positioned within a vicinity of the hub device 201. The speaker 251 and microphone 252 may be coupled to a CODEC 253. The coder/decoder (CODEC) 253 may also be coupled to the processor 202 through a controller 254. The processor 202 may provide audio information captured from the microphone 252 to any electronic device (e.g., server 511 or wireless user device 532) that may facilitate communication with an individual positioned within a vicinity of the hub device 201 through the speaker 251.

The hub device 201 may provide an external audio feedback, for example, playing a greeting, audio message, or ringing a doorbell chime through speaker 251. Moreover, the hub device 201 may provide an internal audio feedback, for example, ringing a digital or mechanical chime or greeting or message. The hub device 201 may communicate with one or more local electronic devices 590, remote computing devices 531, and servers 511 to provide one or more users with remote audio and/or visual feedback.

The hub device 201 may include a controller 254 for controlling the sensors and processing data collected by the sensors, satellite device 360, sensor device 470, electronic device 190, or remote computing device 531. Controller 254 may include a processor, memory/storage device (storing sensor instructions, settings, etc.), and a network module wireless chip for communicating with hub device 201. Controller 254 may send measured/detected environmental conditions and features and individual activity to the processor 202 for further processing. In some exemplary embodiments, the hub device 201 may exclude the controller 254 and function as a sensor only device or satellite device 360 that transfers collected environmental and individual activity in and around a building to another hub device 201 for processing.

In some exemplary embodiments, the hub device 201 includes controller 254 to share or divide processing tasks or priorities of data, video, audio, or environmental sensor data with other hub devices 201. For example, the controller 254 may process certain motion (e.g., individuals, homeowners, pets or animals, etc.) or sounds (e.g., window or door closing or opening, window breaking) and sound an alarm, request verbal input from a user, or trigger an action instead of (or prior to) sending to another hub device 201 for further processing. Similarly, the hub device 201 may process individual and environmental activity prior to sending to a server 511 for further processing if necessary.

The hub device 201 may include and control various sensor components 255 for sensing environmental activity (e.g., temperature, sound, motion, and location of individuals, and their respective changes over time) within a proximity of a building. Sensor components 255 may monitor environmental conditions (e.g., humidity, temperature, pressure, etc.,) by using one or more environmental sensors 256, and individual activity by using one or more motion sensors 257, other sensors 259, and image sensors 258 and microphone 252. Thus, a combination of sensor components 255 may be implemented to provide comprehensive monitoring or improved accuracy in monitoring individual and environmental activity.

The hub device 201 may store collected information from sensor components 255, speaker 251, microphone 252, satellite device 360, sensor device 470, electronic device 190, remote computing devices 431, and server 511 in a database. The database may be stored on additional/external storage 220 of the hub device 201, memory 203, storage 512 of a server 511, or on an application on a remote computing device 531. The space and individual information (e.g., individual activity information) in the database is updated and/or corroborated with the individual and space information acquired by the collected information of the surrounding environment. A user or individual may be prompted to update or approve updating of the database with additional space and individual information acquired by the one or more sensors. The user or individual may further store user preferences and/or classifiers in the database, the user preferences and/or classifiers may include specific instructions or actions based on collected space or individual information, scheduling, time of day, temperature, humidity, etc.

The space and individual information acquired by the hub device 201 from various sources, for example but not limited to, sensor components 255, satellite device 360, sensor device 470, electronic device 190, or remote computing device 531 is compared with classifiers and/or user activity stored in the database, the classifiers and user preferences may then be used by hub device 201 to determine whether to notify other users, call emergency services, or to connect, power, or operate various electronic devices, for example, controlling existing light switches, ceiling fan controls, ceiling fixtures, light fixture controls, dimmers, sound, or motion sensor units, and conventional light switch receptacles, IoT devices, smart home devices, thermostats, cameras, speakers, an intercom, virtual assistants (e.g., a voice operable AI device), etc.

As noted earlier, one or more of the sensor components 255 may be implemented as a separate component from the hub device 201. For example, environmental sensors 256 may detect and collect information about environmental conditions in and around one or more buildings. Environmental sensors 256 may include, for example, temperature sensor, ambient light sensor, humidity sensor, barometer sensor, air quality sensor (e.g., for detecting allergens, gas, pollution, pollen, etc.,), infrared sensor, CO2 sensor, CO sensor, piezoelectric sensor, airflow or airspeed sensor, and the like. The environmental conditions collected by environmental sensors 256 may be used by the processor 202 of the hub device 201 in determining whether to notify a user (e.g., by wireless user device 532). Environmental sensors 256 may include, for example, a motion sensor, an image sensor, a camera, and other sensors (e.g., proximity sensor, occupancy sensor, ambient light sensor). A microphone 252 may also be used to detect features or verify the opening or closing of entry door, movement, body position, or presence of individuals, or any type of environmental activity in and around a building.

In an exemplary embodiment, the hub device 201 comprises one or more motion sensors 257 for detecting motion information. For example, motion sensor 257 may detect moving objects and/or pedestrians. In some exemplary embodiments, the one or more sensors (e.g., motion sensor 257, image sensor 258, etc.) may be positioned along one or more edges of hub device 201. The motion sensor 257 may be a passive infrared motion detector. Infrared motion sensors are also known as PIR (passive infrared) motion sensors or simply PIR sensors. Such detectors have about a 120° arc and about a 50-foot range detection zone. In the case where an increased field of view of motion detection or more accurate motion detection is required, two or more motion detectors may be used.

Suitable alternate motion detectors may also be used, which as ultrasonic, optical, microwave, or video motion detectors. Additional alternative types of motion detectors may also be used to sense intrusion including laser scanning or frequency sensitive detectors, commonly referred to as "glass breaks". Motion sensor 257 may include image sensors having any type of low light level imaging sensors used for surveillance and unmanned monitoring in daylight to complete darkness, for example, low-light complementary metal-oxide-semiconductor (CMOS) or charge-coupled device (CCD) image sensors.

The motion sensor 257 may also be complemented with other devices to aid in detecting motion such as, for example, photocell sensors, cadmium-sulfide (CdS) cells, light-dependent resistors (LDR), and photoresistors. In addition to motion sensors, the photocell sensors may be used to determine if there something in front of a sensor or a series of sensors that block light. The sensitivity of the motion sensor and photocell may be adjusted through, for example, an application on an electronic device (e.g., smart device 534 or laptop 531). Also, a server or application may decide if the situation or application warrants night use or twenty-four-hour operation of motion detection through alternate means such as photocell sensors. If night operation is selected, then the server or application will process detected photocell information to determine if motion was detected.

The hub device 201 may include an image sensor 258 for capturing visual information such as video and still images of the surrounding environment. The image sensor 258 may be coupled to a controller 254 for controlling the camera to capture visual information that may be sent to the processor 202. The controller 254 may be coupled to the processor 202 for processing visual information. The processor 202 may provide visual information captured from the image sensor 258 to any electronic device (e.g., server 511 or remote computing device 531) which may facilitate interaction or communication with an individual or an object positioned within a vicinity of the hub device 201. The image sensor 258 may be any optical instrument for recording or capturing images that may be stored locally, transmitted to another location, or both. The images may be still photographs, or sequences of images forming videos or movies. The image sensor 258 may be any type of camera, for example, high-end professional camera type, digital camera, panoramic camera, fish-eye lens type camera, multi-lens type camera, VR camera, etc.

The hub device 201 may include, or be in communication with, any number of other or additional detectors or sensors, for example, other sensors 259. Examples of other sensors 259 that may be used include, by way of illustration only and not by way of limitation, Time-of-Flight (ToF) sensors, temperature sensors, video cameras, audio recorders, motion sensors, ambient light sensors, light sensors, humidity sensors, smoke detectors, and other sensors, such as for example, an Electric Field Proximity Sensing (EFPS) sensor to determine whether a person or object is nearby that is behind a wall.

The hub device 201 may include a light emitting source 259a may include an LED array, for example, an LED ring. The LED array may include a plurality of RGB lights responsive to input or feedback received from sensor components 255, touch input from a user, or remote or wireless input from a human to machine interface (HMI), for example, instructions from one or more remote computers (e.g., one or more servers, mobile devices, etc.,), or any combination thereof. In some embodiments, the light emitting source 259a may be wirelessly operated or activated by, for example, another hub device 301, another guest or secondary user through the HMI, one or more satellites 160, tags 170, smart home devices, electronic devices, or any combination thereof. The light emitting source 259a may include one or more multicolored LEDs, daylight LEDs, soft light LEDs, animated multicolor LEDs arrays, or any combination thereof, to aid in peaceful sleep. The light emitting source 259a may be recessed within an exterior surface of the hub device 301 or formed along one or more exterior surfaces or curves of hub device 301. The light emitting source 259a may include one or more arrays of light emitting sources (e.g., LEDs) to display animations, cartoons, visual emojis, images, text, brands. In some embodiments, the hub device 301 may allow user customization and/or contain preset, preprogrammed settings for the light emitting source 259a. For example, the light emitting source 259a may be configured, by the hub device 301 or user, to display visual feedback (e.g., themes, colors, images, animations, videos, text, or information) for scheduled events, reminders, appointments, tasks, or seasonal, cultural, historical, economic, socioeconomic, geographic events, or to allow individuals to celebrate or commemorate an event or tradition of cultural or religious significance. Moreover, the user can train the hub device 301 by communicating through one or more remote computing devices (e.g., one or more servers, mobile devices, etc.,), or communicating through audio (e.g., a voice command) or motion (e.g., gesture, body position, or body movement) to configure certain themes, colors and/or interactions with certain times, dates, reminders, etc. The light emitting source 259a may further include a display, for example and not limited to, a resistive touch display or capacitive touch display, a projector display, or other touch or pressure sensitive surface for receiving user input, etc. In some exemplary embodiments, other forms of interaction with the hub device 201, may be by user inputted commands through microphone 252, wireless user device 532, one or more electronic devices 590, remote computing devices 531, server 511, or any combination thereof.

The press feature 259b may be a toggling mechanical button or switch and/or a touch sensitive button or touchpad. In some embodiments, the press feature 259b may include light emitting sources to communicate with the user by, for example, providing visual feedback of button presses, visual feedback for scheduled events, reminders, appointments, tasks, or visual feedback for other programmed or scheduled events or information. The visual feedback may the same, different, preset by the hub device 301 or configured by the user. The user may acknowledge the visual feedback by pressing the press feature 259b, by communicating through one or more remote computing devices (e.g., one or more servers, mobile devices, etc.,), or communicating through audio (e.g., a voice command) or motion (e.g., gesture, body position, or body movement) to acknowledge the feedback.

Figure 3:
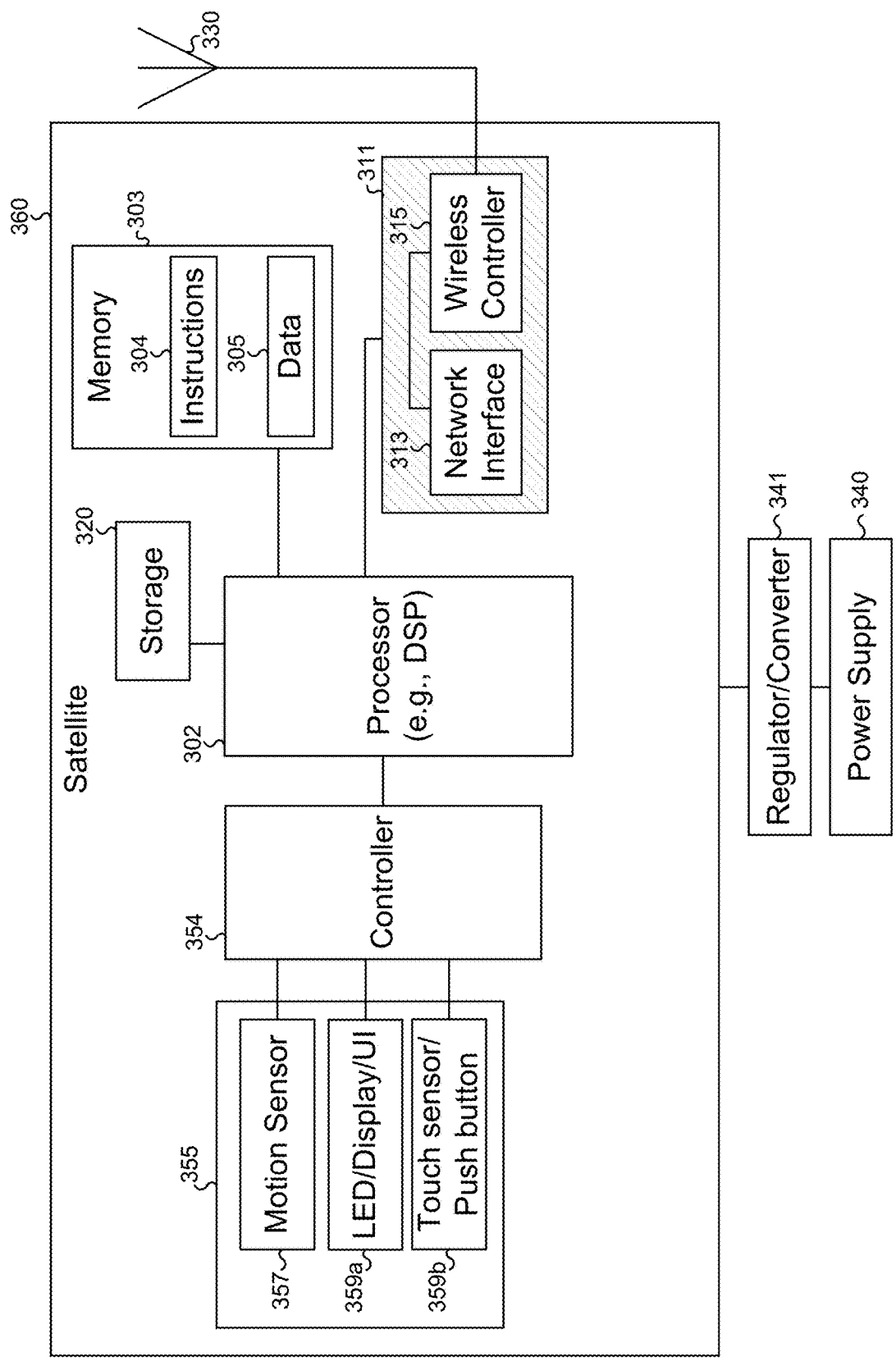
FIG. 3 illustrates conceptually an exemplary satellite device of the monitoring system with which some implementations of the present disclosure may be implemented.

FIG. 3 illustrates conceptually an exemplary satellite device of the monitoring system with which some implementations of the present disclosure may be implemented. As can be seen with reference to FIG. 3, an exemplary satellite device 360 may include one or more of the following: processor 302, memory 303 having instructions 304 and/or data 305, network module 311, network interface 313, wireless controller 315, storage 320, antennas 330, power supply 340, power regulator/convertor 341, and controller 354. The satellite device 360 may further include one or more sensor components 355 that includes at least one motion sensor 357, at least one light emitting sources 359a (e.g., one LED, an array of LEDs, nightlight, etc.,), and one or more press features 359b. The one or more sensor components 355 may be implemented as separate components from the satellite device 360. The satellite device 360 may be any electronic device that transmits signals over a network, such as electronic devices embedded in smart appliances and other smart systems. The satellite device 360 may include various types of computer readable media (e.g., a non-transitory computer-readable medium) and interfaces for various other types of computer readable media. The satellite device 360 may contain one, none, some, or all the components of the hub device 201 as described above and in the present disclosure.

The processor 302 may retrieve and execute instructions 304 and/or data 305 from memory/storage 303 to perform the processes of the present disclosure. Processor 302 may be a single processor, a multi-core processor, or multiple processors in different implementations. Referring to FIGS. 2-6, instructions and data for operating satellite device 360 may be stored on, transmitted from, or received by any computer-readable storage medium (e.g., memory 203, 403 or additional/external storage 220, 420 of hub device 201 or sensor device 470, or memory/storage 512 of one or more servers 511) storing data (e.g., data 305) that is accessible to a processor (e.g., the processor of server 511) during modes of operation of the satellite device 360. The satellite device 360 may access and execute instructions and/or data stored on any remote computing device 531 (e.g., mobile device 532, laptop 533, or tablet 534). The data 305 may be a method instruction for configuring network settings of the satellite device 360 and/or configuring data collection or device settings for various sensor devices 470 and/or electronic devices 590. The method instructions are executable by processor 302. In some embodiments, one or more other satellite devices 560, hub devices 501, sensor device 570, servers 511, electronic devices 590, remote computing devices 531, or any combination thereof, may collect and measure a physical quantity and/or provide instructions for configuring and operating the satellite device 360 and/or communicating between user(s) and other remote, local, and/or wireless electronic devices.

The memory/storage 303 may include a dynamic random-access memory (DRAM) and/or a read-only memory (ROM). Memory/storage 303 may provide a temporary location to store data 305 and instructions 304 retrieved and processed by processor 302. Memory/storage 303 may include a non-volatile read-and-write memory that stores data 305 and instructions 304, even when Wi-Fi/Internet is off, that may be retrieved and processed by processor 302. For example, memory/storage 303 may include magnetic, solid state and/or optical media, memory/storage 303 may be a single or multiple memory units as necessary. The memory/storage 303 stores all collected visual, audio, textual, voice, motion, heat, proximity, etc., information provided directly from one or more satellite devices 560, sensor devices 570, electronic devices 590, or servers 511, or indirectly through a wireless connection to another electronic device(s), sensor device(s) (e.g., a wearable device).

Satellite device 360 couples to a network through a network interface 313. In some embodiments, network interface 313 is a machine-interface. In this manner, the satellite device 360 may be a part of a network of computers, a local area network (LAN), a wide area network (WAN), or an Intranet, or a network of networks, for example, the Internet. A wireless controller 315 may be coupled to the processor 302. The wireless controller 315 may be further coupled to an antenna 380. The network module 311 may be integrated as system-in-package or system-on-chip device and/or collectively defined as having the network interface 313 and wireless controller 315. Network interface 313 and wireless controller 315 integrated into the network module 311 and being coupled to an antenna 380. Any or all components of satellite device 360 may be used in conjunction with the subject disclosure. The network interface 313 may include cellular interfaces, Wi-Fi™ interfaces, Infrared interfaces RFID interfaces, ZigBee interfaces, Bluetooth interfaces, Ethernet interfaces, coaxial interfaces, optical interfaces, or generally any communication interface that may be used for device communication. The satellite device 360 may be configured as a Wi-Fi™ bridge or Wi-Fi™ extender to extend the range of the hub device 201 and consequently connect and collect additional individual and environmental information collected from sensor devices 570, electronic devices 590, servers 511, or remote computing device outside the range of hub device 201, as well as collecting such information indirectly through a wireless connection to another electronic device(s), sensor device(s) (e.g., a wearable device).

The satellite device 360 is powered through a power supply 340. The power supply 340 may include disposable and/or rechargeable batteries (e.g., 3800 mAh rechargeable Li-Polymer battery), existing electrical wiring, a power supply adapter, or any combination thereof. Disposable batteries or rechargeable batteries, for example, nickel cadmium (NiCd), lithium (Li), AA, AAA, and/or rechargeable capacitors, for example, supercapacitors (SC) or ultracapacitors. The power supply 340 may supply power to satellite device 360 by, for example, a power adapter for connecting to an outlet, a solar panels/cell, or any other renewable/alternative power supply source. The satellite device 360 may use multiple battery types, multiple power sources, etc., for example, using a coin cell battery to operate some sensor components 355. Moreover, a converter/regulator 341; transformer or voltage regulator, AC to DC or DC to DC power converter, or frequency converter may be used separately (electrically coupled to the satellite device 360) or integrated within the satellite device 360 to provide adequate input power to the satellite device 360 (e.g., 12 VDC).

The satellite device 360 may include a controller 354 for controlling the sensors and processing data collected by the sensors, other satellite devices 360, sensor devices 470, electronic device 190, or remote computing device 531. Controller 354 may include a processor, memory/storage device (storing sensor instructions, settings, etc.), and a network module wireless chip for communicating with satellite device 360. Controller 354 may send measured/detected environmental conditions and features and individual activity to the processor 302 for further processing. In some exemplary embodiments, the satellite device 360 may exclude the controller 354 and function as a sensor only device or satellite device 360 that transfers collected environmental and individual activity in and around a building to another satellite device 360 for processing.

In some exemplary embodiments, the satellite device 360 includes controller 354 to share or divide processing tasks or priorities of data, video, audio, or environmental sensor data with other satellite devices 360, sensor devices 470, or hub devices 401. For example, the controller 354 may process certain motion (e.g., individuals, homeowners, pets or animals, etc.) or sounds (e.g., window or door closing or opening, window breaking) and sound an alarm, request verbal input from a user, or trigger an action instead of (or prior to) sending to another satellite device 360 for further processing. Similarly, the satellite device 360 may process individual and environmental activity prior to sending to a hub device 201 and/or server 511 for further processing if necessary.

The satellite device 360 may communicate collected information from sensor components 355, other satellite devices 360, sensor device 470, electronic device 190, remote computing devices 431, and server 511 to one or more hub devices 201 and/or one or more satellite devices 360. In some embodiments, the satellite device 360 may store collected information, in part or in whole, from sensor components 355, other satellite devices 360, sensor device 470, electronic device 190, remote computing devices 431, and server 511 in a database prior to or subsequent to communicating the information to one or more hub devices 201 and/or one or more satellite devices 360. The database may be stored on additional/external storage 320 of the satellite device 360, memory 303, storage 512 of a server 511, or on an application on a remote computing device 531. The space and individual information (e.g., individual activity information) in the database is updated and/or corroborated with the individual and space information acquired by the collected information of the surrounding environment. A user or individual may be prompted to update or approve updating of the database with additional space and individual information acquired by the one or more sensors. The user or individual may further store user preferences and/or classifiers in the database, the user preferences and/or classifiers may include specific instructions or actions based on collected space or individual information, scheduling, time of day, temperature, humidity, etc.

The space and individual information acquired by the satellite device 360 from various sources, for example but not limited to, sensor components 355, other satellites 360, sensor device 470, electronic device 190, or remote computing device 531 may be compared with classifiers and/or user activity stored in the database, the classifiers and user preferences may then be used by satellite device 360 to determine whether to communicate the information to one or more hub devices 201, to notify other users, call emergency services, or to connect, power, or operate various electronic devices, for example, controlling existing light switches, ceiling fan controls, ceiling fixtures, light fixture controls, dimmers, sound, or motion sensor units, and conventional light switch receptacles, IoT devices, smart home devices, thermostats, cameras, speakers, an intercom, virtual assistants (e.g., a voice operable AI device), etc.

In an exemplary embodiment, the satellite device 360 comprises one or more motion sensors 357 for detecting motion information. For example, motion sensor 357 may detect moving objects and/or pedestrians. In some exemplary embodiments, the one or more sensors (e.g., motion sensor 357, image sensor 358, etc.) may be positioned along one or more edges of satellite device 360. The motion sensor 357 may be a passive infrared motion detector. Infrared motion sensors are also known as PIR (passive infrared) motion sensors or simply PIR sensors. Such detectors have about a 120° arc and about a 50-foot range detection zone. In the case where an increased field of view of motion detection or more accurate motion detection is required, two or more motion detectors may be used.

Suitable alternate motion detectors may also be used, which as ultrasonic, optical, microwave, or video motion detectors. Additional alternative types of motion detectors may also be used to sense intrusion including laser scanning or frequency sensitive detectors, commonly referred to as "glass breaks". Motion sensor 357 may include image sensors having any type of low light level imaging sensors used for surveillance and unmanned monitoring in daylight to complete darkness, for example, low-light complementary metal-oxide-semiconductor (CMOS) or charge-coupled device (CCD) image sensors.

The motion sensor 357 may also be complemented with other devices to aid in detecting motion such as, for example, photocell sensors, cadmium-sulfide (CdS) cells, light-dependent resistors (LDR), and photoresistors. In addition to motion sensors, the photocell sensors may be used to determine if there something in front of a sensor or a series of sensors that block light. The sensitivity of the motion sensor and photocell may be adjusted through, for example, an application on an electronic device (e.g., smart device 534 or laptop 531). Also, a server or application may decide if the situation or application warrants night use or twenty-four-hour operation of motion detection through alternate means such as photocell sensors. If night operation is selected, then the server or application will process detected photocell information to determine if motion was detected.

The satellite device 360 may include a light emitting source 359*a* may include an LED array, for example, an LED ring. The LED array may include a plurality of RGB lights responsive to input or feedback received from sensor components 355, touch input from a user, or remote or wireless input from a human to machine interface (HMI), for example, instructions from one or more remote computers (e.g., one or more servers, mobile devices, etc.,), or any combination thereof. In some embodiments, the light emitting source 359*a* may be wirelessly operated or activated by, for example, hub device 201, another guest or secondary user through the HMI, one or more satellites 160, tags 170, smart home devices, electronic devices, or any combination thereof. The light emitting source 359*a* may include one or more multicolored LEDs, daylight LEDs, soft light LEDs, animated multicolor LEDs arrays, or any combination thereof, to aid in peaceful sleep. The light emitting source 359*a* may be recessed within an exterior surface of the satellite device 360 or formed along one or more exterior surfaces or curves of the satellite device 360. The light emitting source 359*a* may include one or more arrays of light emitting sources (e.g., LEDs) to display animations, cartoons, visual emojis, images, text, brands. In some embodiments, the satellite device 360 may allow user customization and/or contain preset, preprogrammed settings for the light emitting source 359*a*. For example, the light emitting source 359*a* may be configured, by the satellite device 360 or user, to display visual feedback (e.g., themes, colors, images, animations, videos, text, or information) for scheduled events, reminders, appointments, tasks, or seasonal, cultural, historical, economic, socioeconomic, geographic events, or to allow individuals to celebrate or commemorate an event or tradition of cultural or religious significance. The light emitting source 359*a* may further include a display, for example and not limited to, a resistive touch display or capacitive touch display, a projector display, or other touch or pressure sensitive surface for receiving user input, etc. In some exemplary embodiments, other forms of interaction with the satellite device 360, may be by user inputted commands through microphone 252 to the hub device 201, wireless user device 532, one or more electronic devices 590, remote computing devices 531, server 511, or any combination thereof.

The press feature 359*b* may be a toggling mechanical button or switch and/or a touch sensitive button or touchpad. In some embodiments, the press feature 359*b* may include light emitting sources to communicate with the user by, for example, providing visual feedback of button presses, visual feedback for scheduled events, reminders, appointments, tasks, or visual feedback for other programmed or scheduled events or information. The visual feedback may the same, different, preset by the satellite device 360 or configured by the user. The user may acknowledge the visual feedback by pressing the press feature 359*b*, by communicating through one or more remote computing devices 531 (e.g., one or more servers, mobile devices, etc.,), or communicating through audio (e.g., a voice command) or motion (e.g., gesture, body position, or body movement) to acknowledge the feedback.

Figure 4:
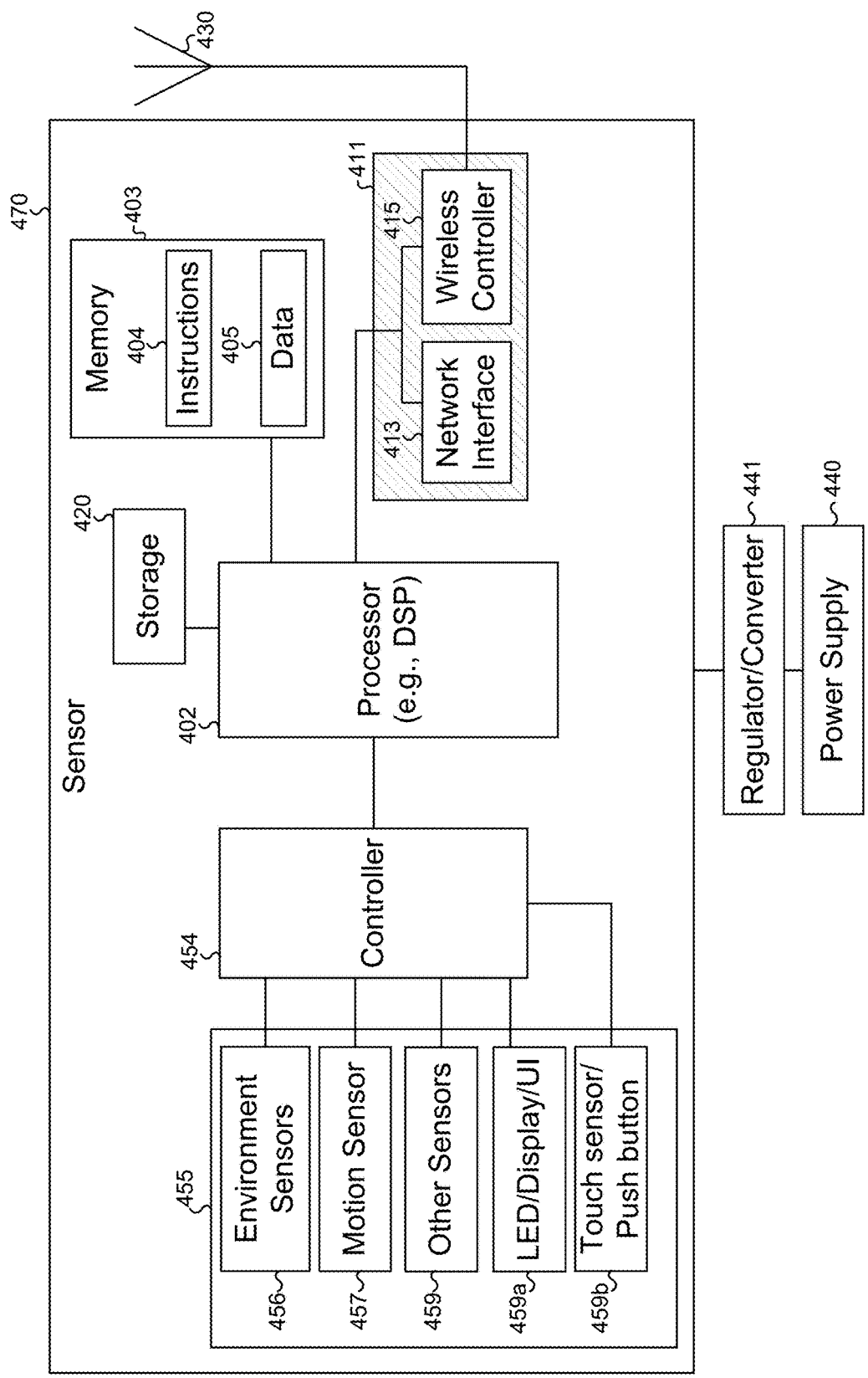
FIG. 4 illustrates conceptually an exemplary sensor device of the monitoring system with which some implementations of the present disclosure may be implemented.

FIG. 4 illustrates conceptually an exemplary sensor device of the monitoring system with which some implementations of the present disclosure may be implemented. As can be seen with reference to FIG. 4, an exemplary sensor device 470 may include one or more of the following: processor 402, memory 403 having instructions 404 and/or data 405, network module 411, network interface 413, wireless controller 415, storage 420, antennas 430, power supply 440, power regulator/convertor 441, and controller 454. The sensor device 470 may further include one or more sensor components 455 that includes at least one environment sensor 456, at least one motion sensor 457, at least one other sensors 459, at least one light emitting sources 459*a* (e.g., one LED, an array of LEDs, nightlight, etc.,), and one or more press features 459*b*. The sensor device 470 may be any electronic device that transmits signals over a network, such as electronic devices embedded in smart appliances and other smart systems. The sensor device 470 may include various types of computer readable media (e.g., a non-transitory computer-readable medium) and interfaces for various other types of computer readable media. The sensor device 470 may contain one, none, some, or all the components of the hub device 201 as described above and in the present disclosure.

The processor 402 may retrieve and execute instructions 404 and/or data 405 from memory/storage 403 to perform the processes of the present disclosure. Processor 402 may be a single processor, a multi-core processor, or multiple processors in different implementations. Referring to FIGS. 2-6, instructions and data for operating sensor device 470 may be stored on, transmitted from, or received by any computer-readable storage medium (e.g., memory 203, 303 or additional/external storage 220, 320 of hub device 201 or satellite device 360, or memory/storage 512 of one or more servers 511) storing data (e.g., data 405) that is accessible to a processor (e.g., the processor of server 511) during modes of operation of the sensor device 470. The sensor device 470 may access and execute instructions and/or data stored on any remote computing device 531 (e.g., mobile device 532, laptop 533, or tablet 534). The data 405 may be a method instruction for configuring network settings of the sensor device 470 and/or configuring data collection or device settings for various sensor devices 470 and/or electronic devices 590. The method instructions are executable by processor 402. In some embodiments, one or more satellite devices 560, hub devices 501, other sensor devices 570, servers 511, electronic devices 590, remote computing devices 531, or any combination thereof, may collect and measure a physical quantity and provide instructions for configuring and operating the sensor device 470 and/or communicating between user(s) and other remote, local, and/or wireless electronic devices.

The memory/storage 403 may include a dynamic random-access memory (DRAM) and/or a read-only memory (ROM). Memory/storage 403 may provide a temporary location to store data 405 and instructions 404 retrieved and processed by processor 402. Memory/storage 403 may include a non-volatile read-and-write memory that stores data 405 and instructions 404, even when Wi-Fi/Internet is off, that may be retrieved and processed by processor 402. For example, memory/storage 403 may include magnetic, solid state and/or optical media, memory/storage 403 may be a single or multiple memory units as necessary. The memory/storage 403 stores all collected visual, audio, textual, voice, motion, heat, proximity, etc., information provided directly from one or more onboard sensors.

Sensor device 470 couples to a network through a network interface 413. In some embodiments, network interface 413 is a machine-interface. In this manner, the sensor device 470 may be a part of a network of computers, a local area network (LAN), a wide area network (WAN), or an Intranet, or a network of networks, for example, the Internet. A wireless controller 415 may be coupled to the processor 402. The wireless controller 415 may be further coupled to an antenna 430. The network module 411 may be integrated as system-in-package or system-on-chip device and/or collectively defined as having the network interface 413 and wireless controller 415. Network interface 413 and wireless controller 415 integrated into the network module 411 and being coupled to an antenna 430. Any or all components of sensor device 470 may be used in conjunction with the subject disclosure. The network interface 413 may include cellular interfaces, Wi-Fi™ interfaces, Infrared interfaces RFID interfaces, ZigBee interfaces, Bluetooth interfaces, Ethernet interfaces, coaxial interfaces, optical interfaces, or generally any communication interface that may be used for device communication.

The sensor device 470 may be powered through a power supply 440. The power supply 440 may include disposable and/or rechargeable batteries (e.g., 4800 mAh rechargeable Li-Polymer battery), existing electrical wiring, a power supply adapter, or any combination thereof. Disposable batteries or rechargeable batteries, for example, nickel cadmium (NiCd), lithium (Li), AA, AAA, and/or rechargeable capacitors, for example, supercapacitors (SC) or ultracapacitors. The power supply 440 may supply power to sensor device 470 by, for example, a power adapter for connecting to an outlet, a solar panels/cell, or any other renewable/alternative power supply source. The sensor device 470 may use multiple battery types, multiple power sources, etc., for example, using a coin cell battery to operate some sensor components 455. Moreover, a converter/regulator 441; transformer or voltage regulator, AC to DC or DC to DC power converter, or frequency converter may be used separately (electrically coupled to the sensor device 470) or integrated within the sensor device 470 to provide adequate input power to the sensor device 470 (e.g., 12 VDC). In some embodiments, the sensor device 470 may be a passive device that is powered remotely upon receiving electromagnetic waves that, for example, charge a capacitor to supply power for the sensor device 470.

The sensor device 470 may include a controller 454 for controlling the sensors and processing data collected by the sensors, other satellite devices 460, sensor devices 470, electronic device 190, or remote computing device 531. Controller 454 may include a processor, memory/storage device (storing sensor instructions, settings, etc.), and a network module wireless chip for communicating with sensor device 470. Controller 454 may send measured/detected environmental conditions and features and individual activity to the processor 402 for further processing. In some exemplary embodiments, the sensor device 470 may exclude the controller 454 and function as a sensor only device or sensor device 470 that transfers collected environmental and individual activity in and around a building to a hub device 201 a satellite device, and/or relay to another sensor device 470 for processing.

In some exemplary embodiments, the sensor device 470 includes controller 454 to share or divide processing tasks or priorities of data, video, audio, or environmental sensor data with other sensor devices 470, satellite devices 360, or hub devices 401. For example, the controller 454 may process certain motion (e.g., individuals, homeowners, pets or animals, etc.) or sounds (e.g., window or door closing or opening, window breaking) and sound an alarm, request verbal input from a user, or trigger an action instead of (or prior to) sending to another sensor device 470 for further processing. Similarly, the sensor device 470 may process individual and environmental activity prior to sending to a hub device 201 and/or server 511 for further processing if necessary.

The sensor device 470 may include and control various sensor components 455 for sensing environmental activity (e.g., temperature, sound, motion, and location of individuals, and their respective changes over time) within a proximity of a building. Sensor components 455 may monitor environmental conditions (e.g., humidity, temperature, pressure, etc.,) by using one or more environmental sensors 456, and individual activity by using one or more motion sensors 457, and other sensors 459. Thus, a combination of sensor components 455 may be implemented to provide comprehensive monitoring or improved accuracy in monitoring individual and environmental activity. In some embodiments, the sensor device 470 includes only a single sensor component (e.g., a motion sensor, a temperature sensor, etc.), which is operable to produce or more particular measurements.

The sensor device 470 may communicate collected information from sensor components 455, satellite devices 460, other sensor devices 470, electronic devices 190, remote computing devices 431, and servers 511 to one or more hub devices 201 and/or one or more satellite devices 460. In some embodiments, the sensor device 470 may store collected information, in part or in whole, from sensor components 455, other satellite devices 460, sensor device 470, electronic device 190, remote computing devices 431, and server 511 in a database prior to, or subsequent to, communicating the information to one or more hub devices 201 and/or one or more satellite devices 460. The database may be stored on additional/external storage 420 of the sensor device 470, memory 403, storage 512 of a server 511, or on an application on a remote computing device 531.

Environmental sensors 456 may detect and collect information about environmental conditions in and around one or more buildings. Environmental sensors 456 may include, for example, temperature sensor, ambient light sensor, humidity sensor, barometer sensor, air quality sensor (e.g., for detecting allergens, gas, pollution, pollen, etc.,), infrared sensor, $CO_2$ sensor, CO sensor, piezoelectric sensor, airflow or airspeed sensor, and the like. The environmental conditions collected by environmental sensors 456 may be used by the processor 202 of the hub device 201 in determining whether to notify a user (e.g., by wireless user device 532). Environmental sensors 456 may include, for example, a motion sensor, an image sensor, a camera, and other sensors (e.g., proximity sensor, occupancy sensor, ambient light sensor).

In an exemplary embodiment, the sensor device 470 comprises one or more motion sensors 457 for detecting motion information. For example, motion sensor 457 may detect moving objects and/or pedestrians. In some exemplary embodiments, the one or more sensors (e.g., motion sensor 457, image sensor 458, etc.) may be positioned along one or more edges of sensor device 470. The motion sensor 457 may be a passive infrared motion detector. Infrared motion sensors are also known as PIR (passive infrared) motion sensors or simply PIR sensors. Such detectors have about a 120° arc and about a 50-foot range detection zone. In the case where an increased field of view of motion detection or more accurate motion detection is required, two or more motion detectors may be used.

Suitable alternate motion detectors may also be used, which as ultrasonic, optical, microwave, or video motion detectors. Additional alternative types of motion detectors may also be used to sense intrusion including laser scanning or frequency sensitive detectors, commonly referred to as "glass breaks". Motion sensor 457 may include image sensors having any type of low light level imaging sensors used for surveillance and unmanned monitoring in daylight to complete darkness, for example, low-light complementary metal-oxide-semiconductor (CMOS) or charge-coupled device (CCD) image sensors.

The motion sensor 457 may also be complemented with other devices to aid in detecting motion such as, for example, photocell sensors, cadmium-sulfide (CdS) cells, light-dependent resistors (LDR), and photoresistors. In addition to motion sensors, the photocell sensors may be used to determine if there something in front of a sensor or a series of sensors that block light. The sensitivity of the motion sensor and photocell may be adjusted through, for example, an application on an electronic device (e.g., smart device 534 or laptop 531). Also, a server or application may decide if the situation or application warrants night use or twenty-four-hour operation of motion detection through alternate means such as photocell sensors. If night operation is selected, then the server or application will process detected photocell information to determine if motion was detected.

The sensor device 470 may include any number of other or additional detectors or sensors, for example, other sensors 459. Examples of other sensors 459 that may be used include, by way of illustration only and not by way of limitation, Time-of-Flight (ToF) sensors, temperature sensors, video cameras, audio recorders, motion sensors, ambient light sensors, light sensors, humidity sensors, smoke detectors, and other sensors, such as for example, an Electric Field Proximity Sensing (EFPS) sensor to determine whether a person or object is nearby that is behind a wall.

The sensor device 470 may include a light emitting source 459a may include an LED array, for example, an LED ring. The LED array may include a plurality of RGB lights responsive to input or feedback received from sensor components 455, touch input from a user, or remote or wireless input from a human to machine interface (HMI), for example, instructions from one or more remote computers (e.g., one or more servers, mobile devices, etc.,), or any combination thereof. In some embodiments, the light emitting source 459a may be wirelessly operated or activated by, for example, hub device 201, another guest or secondary user through the HMI, one or more satellites 160, tags 170, smart home devices, electronic devices, or any combination thereof. The light emitting source 459a may include one or more multicolored LEDs, daylight LEDs, soft light LEDs, animated multicolor LEDs arrays, or any combination thereof, to aid in peaceful sleep. The light emitting source 459a may be recessed within an exterior surface of the sensor device 470 or formed along one or more exterior surfaces or curves of the sensor device 470. The light emitting source 459a may include one or more arrays of light emitting sources (e.g., LEDs) to display animations, cartoons, visual emojis, images, text, brands. In some embodiments, the sensor device 470 may allow user customization and/or contain preset, preprogrammed settings for the light emitting source 459a. For example, the light emitting source 459a may be configured, by the sensor device 470 or user, to display visual feedback (e.g., themes, colors, images, animations, videos, text, or information) for scheduled events, reminders, appointments, tasks, or seasonal, cultural, historical, economic, socioeconomic, geographic events, or to allow individuals to celebrate or commemorate an event or tradition of cultural or religious significance. The light emitting source 459a may further include a display, for example and not limited to, a resistive touch display or capacitive touch display, a projector display, or other touch or pressure sensitive surface for receiving user input, etc. In some exemplary embodiments, other forms of interaction with the sensor device 470, may be by user inputted commands through microphone 252 to the hub device 201, wireless user device 532, one or more electronic devices 590, remote computing devices 531, server 511, or any combination thereof.

The press feature 459b may be a toggling mechanical button or switch and/or a touch sensitive button or touchpad. In some embodiments, the press feature 459b may include light emitting sources to communicate with the user by, for example, providing visual feedback of button presses, visual feedback for scheduled events, reminders, appointments, tasks, or visual feedback for other programmed or scheduled events or information. The visual feedback may the same, different, preset by the sensor device 470 or configured by the user. The user may acknowledge the visual feedback by pressing the press feature 459b, by communicating through one or more remote computing devices 531 (e.g., one or more servers, mobile devices, etc.,), or communicating through audio (e.g., a voice command) or motion (e.g., gesture, body position, or body movement) to acknowledge the feedback.

To minimize power consumption, hub device 201, satellite device 360, sensor device 470, and cellular pendant 180 may use GPS intermittently without constant polling to minimize power usage. Moreover, additional batteries (e.g., coin-cell battery) may be used as a dedicated source of power for one or more sensors and GPS. Further, low power Extended Discontinuous Reception (EDRX) may be used for out of band signaling.

Figure 5:
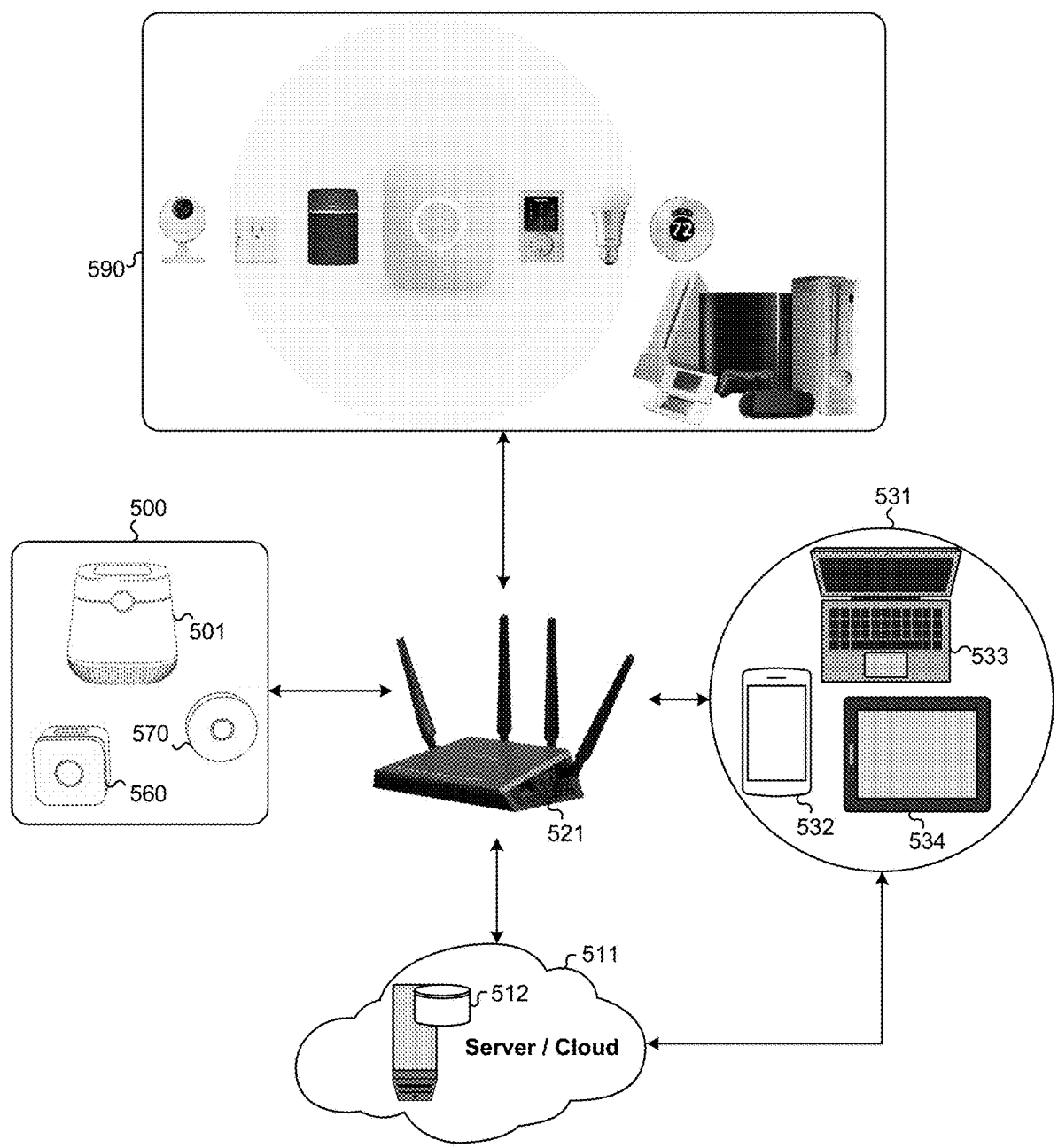
FIG. 5 illustrates an exemplary embodiment of the monitoring system of FIGS. 1-4 communicating with other smart devices or remote computing devices.
Figure 6:
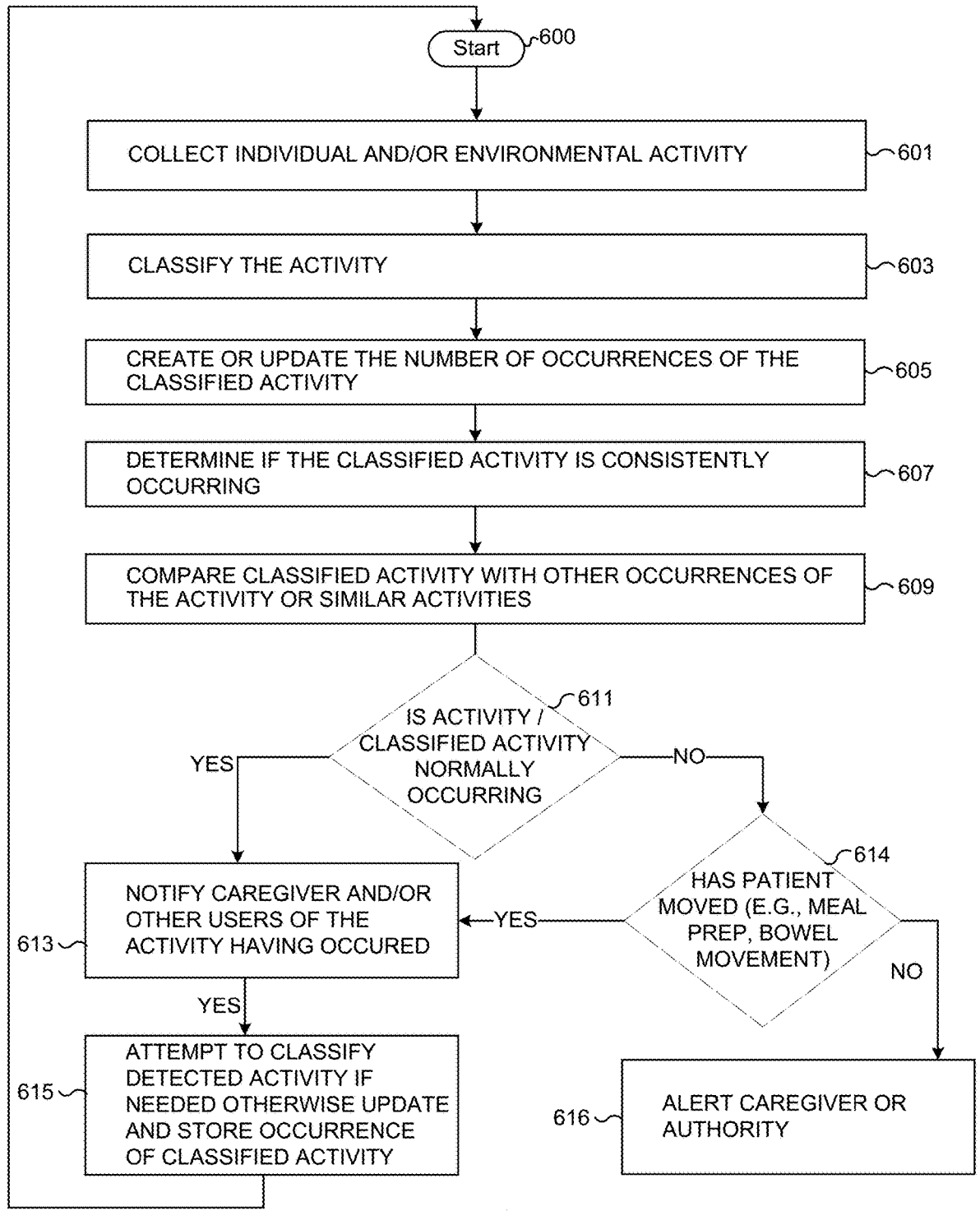
FIG. 6 is a flow chart illustrating an exemplary method of communication of the exemplary hub within the exemplary network environment of FIG. 1.

FIG. 5 illustrates an exemplary embodiment of the monitoring system of FIGS. 1-4 communicating with other smart devices or remote computing devices. As can be seen with reference to FIG. 5, an exemplary embodiment of monitoring system 500 (hub device 501, one or more satellite devices 560, and one or more sensor devices 570) (hereafter "monitoring system 500"). In the following exemplary embodiments, the description of the monitoring system 500 may refer to one of the devices, for example, the hub device 501 notifying the user of individual and/or environmental activity or the satellite device 560 notifying the user (e.g., wireless device 532) and hub device 501 of an individual and/or environmental activity. Alternatively, the monitoring system 500 may refer to the group of devices working together, for example, the satellite device 560 working together with the hub device 501 to notify the user of an individual and/or environmental activity.

The sensor devices 570 as described in the present disclosure may be configured to measure only one physical quantity, for example, the sensor device 570 may include only a motion sensor. In some embodiments, the sensor device 570 may be configured to measure a plurality of physical quantities, for example, the sensor device 570 may include an ambient light sensor, a temperature sensor, an occupancy sensor, and a motion sensor. In some embodiments, several sensor devices 570 may be placed throughout the building to provide an array of measurements throughout the building that a caregiver may wish to monitor. The array of sensor devices 570 may then consistently collect and measure the same physical quantity that may be relayed to one or more hub devices 501 (or a remote computing device) for further processing. The redundancy of measurements collected by the sensor devices 570 may facilitate both redundancy in data collection (e.g., measuring and confirming human movement in the building) and a heatmap of where activities often or seldom occur in the building. This information may provide caregivers with invaluable information on where to place sensor devices 570 in and around the building and what activity to collect (i.e., what type of sensor devices 570 to place in a space).

Further, the hub device 501 or any other component of the monitoring system 500 (e.g., one or more satellite devices 560, one or more sensor devices 570, etc.,) can process the collected activity information without sharing or distributing the information to a server 511 or remote computing device 531 to further maintain privacy. In some embodiments, processing of measured physical quantities can be done within the building through edge computing (i.e., without going to the server 511) to remove the "noise" and produce the results. The caregiver or user selectively choose sensor devices 570 to collect pertinent information about the individual/patient that is processed by the hub device 501 and/or one or more components of the monitoring device 500.

Moreover, the sensor device 570 may be configured to turn off or going into low power mode in the absence of information or activity, in collection of activity, or in transmission of activity in order to save battery life or reduce power consumption. For example, audio and video broadcasting may be paused, stopped, compressed or down-sampled, or broadcasted at lower resolutions or less frequently from one or more sensor devices 570 to one or more satellites 560 and/or hub devices 501. The sensor devices 570 may then become active when needed or when one or more specific activities occur. As another example, sensor devices 570 may include one or more accelerometers configured to run at low speeds (e.g., 25 Hz) and generate an interrupt, when there is sudden motion, the accelerometer may turn the sensor device 570 to full power, when there is lack of motion from the accelerometer the sensor device 570 may power down to, for example, run only inertial measurement units (IMUs). The interrupt line may be tied to the IMU and to the press button on any component of the monitoring devices 500, and any such component of the monitoring device 500 may power up if either IMU or press button sends an interrupt signal.

In some exemplary embodiments, the monitoring system 500 may be linked through Wi-Fi, LAN, WAN, Bluetooth, two-way pager, cellular connection, etc., to a transmitter (e.g., wireless user devices 532, or remote computing device 531). The monitoring system 500 may learn user habits, patterns, and behavior by communicating with one or more electronic devices 590, remote computing devices 531, and servers 511 through, for example, a wireless router 521.

The monitoring system 500 may comprise of wirelessly communicating with one or more local electronic devices 590, remote computing devices 531, and servers 511 through, for example, a wireless router 521. The local electronic devices 590 may include, for example, healthcare or caregiver devices (e.g., scale, blood pressure monitoring device, oximeter, spirometer, electrogram monitoring device, suctioning device, oxygen machine or mask, etc.,), IP cameras, smart outlets, smart switches, smart lightbulbs, smart locks, smart thermostats, video game consoles and smart TVs, smart blinds, garage door monitoring and controlling devices, smart refrigerators, smart washer/dryer, smart devices powered on solar energy, etc. and the like. The monitoring system 500 may also connect to laptops 533, portable devices 534, wireless user device 532, and server 511 and/or server storage 512.

The monitoring system 500 may collect, classify, store, and process user habits, patterns, and behavior to predict and/or learn appropriate actions based on user interactions with the monitoring system 500, electronic devices 590, remote computing devices 531, and servers 511. For example, the monitoring system 500 may collect and process user interactions with, for example, one or more sensor modules 570, electronic devices 590, server 511, transmitter (e.g., wireless user device 280) status and location, or user(s) interaction with the sensor modules 570, electronic devices 590, or any combination of the above.

The monitoring system 500 may communicate user interactions, habits, patterns, and behavior to a server 511, electronic devices 590, remote computing devices 531, or the like for further processing. For example, hub device 501 may activate or operate satellite device 560 or sensor device 570 at certain times based on scheduling or user interaction to collect and process user interactions, habits, patterns, and behavior.

Moreover, user interactions may be classified, cataloged and/or stored in one or more databases (e.g., hub device storage 502, or server storage 512, etc.,) for mapping out user habits, patterns, and behavior to predict and/or learn appropriate actions and responses that may be taken by the monitoring system 500, server 511, and/or communicated by the monitoring system 500 or server 511 to one or more local electronic devices 590, or remote computing devices 531 for taking one or more appropriate actions.

For example, the monitoring system 500 may notify a user of the location of the transmitter when a detected user activity conflicts with the status or location of the transmitter or with the user pattern or habit. The user activity may be collected by the monitoring system 500 and/or one or more local electronic devices 590, or remote computing devices 531. For example, the monitoring system 500 may notify a user by playing an audio message when the user needs to take their medication, meal prep, or perform a daily activity or exercise.

In some exemplary embodiments, components of the monitoring system 500 may include one or more communication modules for communicating wirelessly (e.g., ESP-Now, Bluetooth, Wi-Fi, etc.,) between one or more sensor devices 570, satellite devices 560, and hub devices 501, and/or with one or more remote computing devices 531, servers 511, local electronic devices 590, or any other electronic device mentioned above, to further improve efficiency in the monitoring system 500.

The one or more communications modules may comprise of, for example, a basic low power communications module to communicate with and between components of the monitoring system 500, and more robust or higher power communications module to communicate with other electronic devices 590, connect to the internet, or stream or distribute audio, visual, or motion information through a P2P or direct connection to other electronic devices 590. The data/audio/video sent by the satellite device 560 to the hub device 501 may be sent as an uncompressed data/audio/video file, the hub device 501 may then compress the audio/video file and send to a server 511.

The monitoring system 500 may include a tamper-proof mechanism that may activate the monitoring system 500 image sensor 258 and/or one or more cameras 190D to record video and stream to one or more remote computing devices 531, servers 511, or local electronic devices 590 when the housing or parts of the housing (e.g., battery cover) of any component of the monitoring system 500 is tampered with or damaged, and/or when entry door or windows are broken (e.g., opening of entry door or glass break sound detection).

Moreover, the monitoring system 500 may include a night LED that may operate based on the time in the time zone of installation to provide better lighting conditions for collecting video at night and/or to provide a convenient night light function in the entryway to the building for the visitor or owner.

In some exemplary embodiments, the hub device 501 or satellite device 560 may temporarily store data/video/audio in additional/external storage module 220, 320 when the access point (e.g., router) loses internet connection, or when one or more components of the monitoring system 500 loses network connectivity.

Furthermore, in some exemplary embodiments, components of the monitoring system 500 may be in a normally dormant state (e.g., ECO Mode, Sleep Mode, etc.,). For example, the sensor device 570 and/or satellite device 560 may be off or substantially off (e.g., low power mode) until motion, sound, or a finger press triggers the device to turn to full power mode. Moreover, in some exemplary embodiments, the housing of any one of the components of the monitoring system may include a resistive or capacitive touch sensor and fingerprint sensor formed on or outside of one or more as a manual push button and fingerprint reader.

Once activated by voice command, body posture, or gesture, the monitoring system 500 may attempt to initiate an audio or video call, and/or an audio or video intercom session. The monitoring system 500 may collect the individual conversation or activity and send the communication as a live audio or video stream or recorded video clip or audio clip to one or more servers 511, remote computing devices 531, or local electronic devices 590, or any combination thereof. The communication will initiate a video or audio teleconference with a user, using the speaker 251, microphone 252, and image sensor 258. The video or audio teleconference may be terminated when the individual in front of the entry door leaves, or when the user terminates video or audio teleconference through, for example, an interaction with wireless user device 532 (e.g., finger press, eye motion, or other control command).

The monitoring system 500 may be configured to wirelessly communicate and cooperate with local electronic devices 590 in real-time based on collected individual and/or environmental activity or stored visual, motion, audio, individual and/or environmental information in the hub device storage 202 or server storage 512. The processor 202, controller 254, and/or server 511 may operate the hub device 501 to play a digital or analog chime, a greeting, or collect environmental activity (e.g., video, audio, temperature, etc.,) to send to a computing device (e.g., local electronic devices 590, remote computing devices 531, server 511, etc.,) based on triggered individual and/or environmental activity as collected by the monitoring system 500. The user may further define zones of activity for collecting, classify, and storing information or triggering notifications for users, for example, a user may select or define areas or regions within a space of a building by an image or live video of the environment, or proximity of the activity from the device of the monitoring system 500.

Other local electronic devices 590 (e.g., security camera, thermostat, smoke detector, smart lock, smart TV, etc.,) may cooperate with or supplement sensor device 570 to provide comprehensive information of environmental activity around the building, or one or more zones around the building. In some exemplary embodiments, the security camera 190D may add additional monitoring (data, audio, or video) information to allow one or more hub devices 501 to collect, filter out, or learn a tenant's activity around the building.

The monitoring system 500 may be configured to communicate between the above local electronic devices 590 (e.g., security devices, smart thermostat, smart devices, or smart appliances) by sending and retrieving proximity information, schedule information, textual (e.g., email, SMS, MMS, text, etc.,), visual, motion, or audio information, as well as user access information shared between electronic devices. For example, the monitoring system 500 may be configured to be notified by these smart devices of exterior weather conditions, user's health or vital conditions, vehicle or user location, air quality, allergens/pollen, peak hours, etc. Notification may be made through text, email, visual, or audio information provided by the hub device 501 to remote computing devices 531, server 511, and/or local electronic devices 590 or any other electronic device mentioned above.

In this way, the monitoring system 500 acts as a hub for collecting and processing environmental activity from other electronic devices, classifying the frequency, pattern, and/or time of occurrence, then prompting the server 511 or remote computing device 531 for control instructions to play an audio file, message, video, or to collect environmental activity (e.g., data, video, audio, temperature, etc.,) to send to a computing device (e.g., base module 301, local electronic devices 590, remote computing devices 531, server 511, etc.). The monitoring system 500 may also operate local electronic devices 590 based on classifier, user conditions or preferences. For example, if a user must perform a daily activity, (e.g., exercise or walk), the monitoring system 500 may set electronic devices 590 to relay the information by playing a message or displaying a sequence or colors to indicate a specific daily activity needs to be performed and sensor devices 570 and/or electronic devices 590 will listen and collect motion and/or audio information within the building to confirm the daily activity was performed.

The monitoring system 500 may be communicatively coupled to and controlled, programmed, or reprogrammed by local electronic devices 590 in the building, remote computing devices 531, or by one or more servers 511 to collect such data or collect additional data.

The monitoring system 500 may also include a cellular pendant 180 with a panic button that a user may carry to operate local electronic devices 590 (e.g., a smart lock for an entry door) or contact emergency services. In some exemplary embodiments, the pendant 180 may be, for example and not limited to, a RFID card or RFID device with an accelerometer that may be attached to a remote computing device 531. In some exemplary embodiments, the monitoring system 500 may be programmed by the user to respond to the pendant 180 based on a schedule, geo-location of a user, user preferences, user mobility, user falling, etc. Responses may include any combination of, operating one or more hub devices 501, one or more entry point devices 260, operating local electronic device 590, calling caregivers and/or emergency services, and the like.

The monitoring system 500 may use a shared IP or dedicated IP. The monitoring system 500 having a fixed or static IP may benefit from numerous advantages, such as but not limited to, less downtime or power consumption from IP address refreshes, Private SSL Certificate, Anonymous FTP, Remote access, and access when the domain name is inaccessible.

The monitoring system 500 may further be communicably coupled to one or more door sensors and window sensors. The door sensors and window sensors may notify the monitoring system 500 in the event of a window or door opening, the monitoring system 500 may then turn on and begin capturing audio and video of the event and concurrently or subsequently notify one or more local electronic devices 590, remote computing devices 531, servers 511, etc.

FIG. 6 is a flow chart illustrating an exemplary method of classifying individual activity and corresponding environmental activity. The exemplary method is provided by way of example, as there are a variety of ways to carry out the method. Each box shown in FIG. 6 represents one or more processes, methods or subroutines, carried out in the exemplary method. FIGS. 1-5 show exemplary embodiments of carrying out the method of FIG. 6. The exemplary method may begin at box 600. Further for explanatory purposes, the boxes of the example process 600 are described herein as occurring in serial, or linearly. However, multiple boxes of the example process 600 may occur in parallel. In addition, the boxes of the example process 600 may be performed a different order than the order shown and/or one or more of the boxes of the example process 600 may not be performed.

The exemplary method of FIG. 6 includes collecting individual and/or environmental activity in and/or around a building (box 601). The collected activity may be a new activity, a matching stored or previously occurred activity, or similar to a new or previously stored activity.

The method further includes classifying the activity (box 603), classification may include comparing the collected activity (sensor information) with a database of various measured physical quantities that have been used to define a previous activity or a set of activities.

The method further includes creating or updating the number of occurrences of the collected activity, if the collected activity matches a classified activity the detected activity will be added to the database as an additional occurrence of the classified activity (box 605).

The method further includes determining if the classified activity is consistently occurring (box 607). For example, the collected sensor information may be used to determine whether the user engaging in meal preparation on a daily basis. One or more sensor device 170 may be placed in the kitchen to measure movement in the kitchen, the hub device 101 determining whether this movement occurs on a daily basis, at specific times (e.g., morning, afternoon, and in the evenings), with specific sound signatures (e.g., faucet running, refrigerator opening, noises from pots or pans, etc.,) to classify the activity/event as meal preparation.

The method further includes comparing the classified activity with other occurrences of the activity or similar activities (box 609). For example, if the sound of pots and pans are not detected but instead the sound of a microwave is detected, the hub device 101 may continue to classify the event as meal preparation.

The method further includes determining whether the detected activity is a normally occurring activity (box 611). If the detected activity is normally occurring, the caregiver and/or other users of the activity are notified (box 613). The activity is then evaluated to determine if the activity needs to be classified as a new activity or otherwise the activity is stored in the database as an occurrence of a classified activity (box 615).

However, if the detected activity is not normally occurring (box 611), the patient's activities are evaluated to determine whether they had recently moved, made a meal, and/or had a bowel movement (box 614). If it is determined the patient has not been moving within a predetermined amount of time, the caregiver(s) and/or authorities are notified (box 616). If it is determined the patient has been moving, the caregiver and/or other users of the activity are notified (box 613). The activity is then evaluated to determine if the activity needs to be classified as a new activity or otherwise the activity is stored in the database as an occurrence of a classified activity (box 615).

Figure 7:
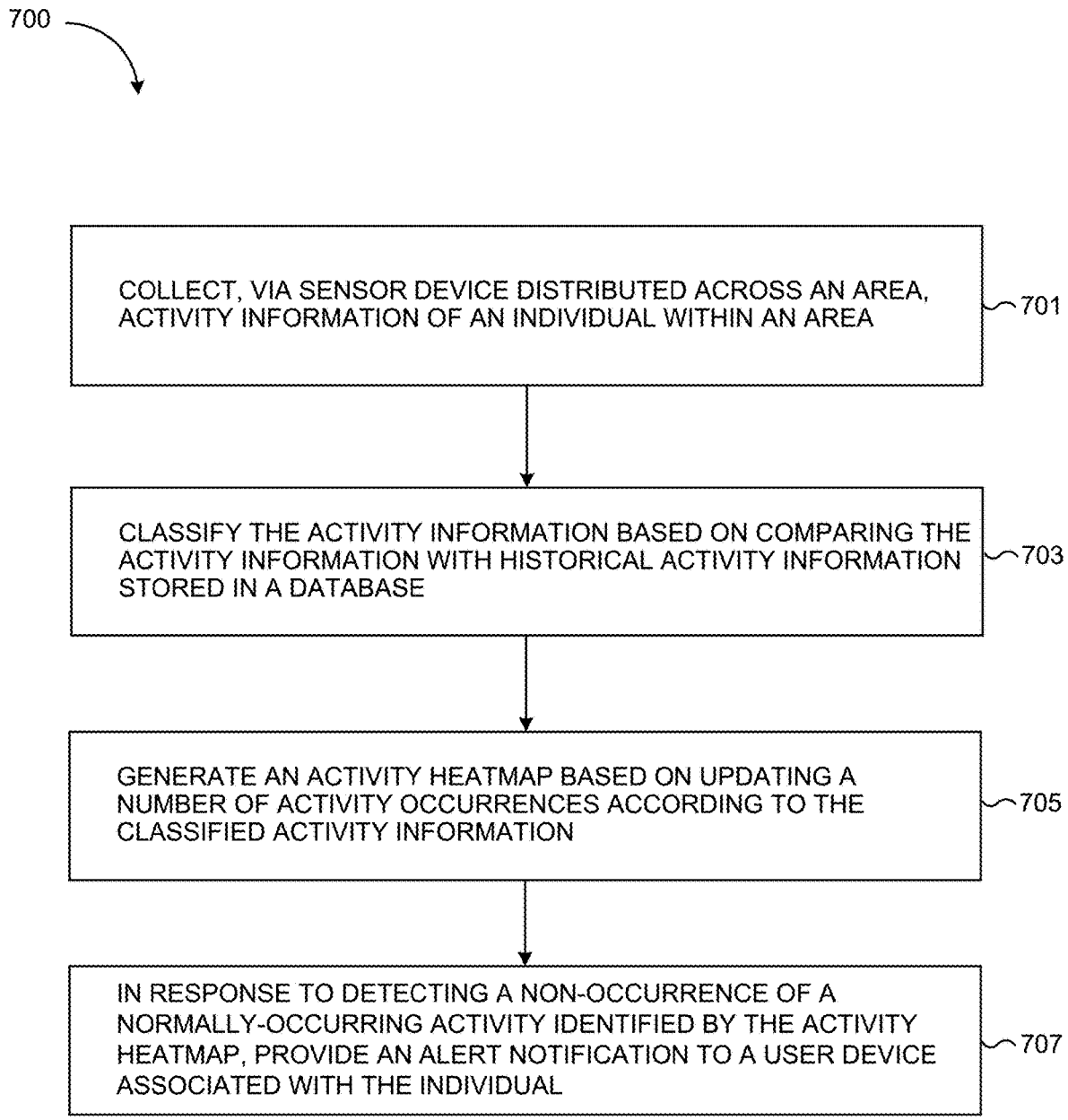
FIG. 7 is a flow chart illustrating an exemplary method for a monitoring system, according to some implementations of the present disclosure.

FIG. 7 is a flow chart illustrating an exemplary method for a monitoring system. The exemplary method is provided by way of example, as there are a variety of ways to carry out the method. Each box shown in FIG. 7 represents one or more processes, methods or subroutines, carried out in the exemplary method. For explanatory purposes, the boxes of the example process 700 are described herein as occurring in serial, or linearly. However, multiple boxes of the example process 700 may occur in parallel. In addition, the boxes of the example process 700 may be performed a different order than the order shown and/or one or more of the boxes of the example process 700 may not be performed.

The exemplary method of FIG. 7 includes collecting, via a plurality of sensor devices of a monitoring system that are distributed across an area, activity information of an individual within an area (box 701). In some embodiments, collecting the activity information includes capturing, by the plurality of sensor devices, sensor data that includes the activity information of the individual within the area; receiving, by a satellite device of the monitoring system, sensor data that includes the activity information from the plurality of sensor devices; and providing, by the satellite device, the activity information.

The method further includes classifying the activity information based on comparing the activity information with historical activity information stored in a database (box 703). In some embodiments, the activity information includes at least one of a temperature, humidity, sounds, or airflow of the area and individual information that includes a medical condition or an amount of daily activity of the individual.

The method further includes generating an activity heatmap based on updating a number of activity occurrences according to the classified activity information (box 705). In some embodiments, the activity heatmap is generated in a memory storage that is partitioned into rows and columns. Each row of the memory storage corresponds to a different sensor device from which the activity information originates, and each column of the memory storage corresponds to a different time period with which the activity information is associated.

The method further includes, in response to detecting a non-occurrence of a normally-occurring activity identified by the activity heatmap, providing an alert notification to a user device associated with the individual (box 707). In some embodiments, detecting the non-occurrence of the normally-occurring activity is performed using a deterministic analysis based on the activity heatmap and detections obtained from one or more of the plurality of sensor devices.

In some embodiments, the method further includes providing placement information that indicates where to place the plurality of sensor devices within the area based on the activity heatmap. In some embodiments, the method further includes dynamically including a new sensor device with the plurality of sensor devices based on in response to the new sensor device broadcasting a signal on a monitored open receive channel; and collecting activity information of the individual from the new sensor device.

The following technical solutions may be implemented by some preferred embodiments.

1) A monitoring system, comprising: a plurality of sensor devices each configured to collect sensor data from a respective environment, wherein the plurality of sensor devices are spread across multiple locations within an area; one or more satellite devices each configured to facilitate wireless communication between the plurality of sensor devices and a hub device of the monitoring system; and the hub device in communication with the one or more satellite devices. The hub device is configured to: dynamically add a new sensor device to the plurality of sensor devices; receive, from the one or more satellite devices, sensor data that originates from the plurality of sensor devices; generate an activity record of the area based on classifying activity information captured by the sensor data; and in response to determining that an occurrence or non-occurrence of a particular activity deviates from the activity record in a particular sensor data, transmit an alert notification to a user device.

2) The monitoring system of solution 1, wherein the one or more satellite devices are each configured to communicate with the plurality of sensor devices via a first communication protocol, and communicate with the hub device via a second communication protocol.

3) The monitoring system of any of solution 1 or solution 2, wherein dynamically adding the new sensor device to the plurality of sensor devices includes building a whitelist that identifies each of the plurality of sensor devices.

4) The monitoring system of any of solutions 1-3, wherein the activity record comprises a heatmap that identifies locations and frequencies of activity occurrences.

5) The monitoring system of any of solutions 1-4, wherein the plurality of sensor devices includes a pendant device carried by an individual and configured for cellular network communication.

6) The monitoring system of any of solutions 1-5, wherein the activity record is specific to an individual being monitored by the monitoring system, and wherein the user device to which the alert notification is transmitted is associated with a caregiver responsible for the individual and located remote to the area.

7) The monitoring system of any of solutions 1-6, wherein the plurality of sensor devices includes a particular sensor device comprising: a wireless controller via which the particular sensor device communicates with the one or more satellite devices; a microcontroller unit configured to execute instructions to operate the wireless controller; and a microelectromechanical inertial measurement unit (IMU) coupled to the microcontroller unit. The microelectromechanical IMU is configured to provide a digital input to the microcontroller unit to change a state of the microcontroller unit to a powered-on state in response to a movement effected on the microelectromechanical IMU.

8) The monitoring system of solution 7, wherein the microelectromechanical IMU is coupled to a chip enable pin of the microcontroller unit that is configured to maintain the microcontroller unit in a powered-off state until the microelectromechanical IMU provides the digital input to change the state of the microcontroller units.

9) The monitoring system of any of solutions 1-8, wherein the hub device is configured to dynamically add the new sensor device in response to the new sensor device broadcasting a signal on an open receive channel monitored by the hub device and further in response to receiving an acknowledgment to a query transmitted by the hub device to the user device, the query identifying the new sensor device.

10) The monitoring system of any of solutions 1-9, wherein the hub device is configured to generate the activity record in a memory storage that is partitioned into rows and columns, wherein each row of the memory storage corresponds to a different sensor device from which the hub device receives sensor data, and wherein each column of the memory storage corresponds to a different time period in which the hub device receives sensor data from the plurality of sensor devices.

11) The monitoring system of any of solutions 1-10, wherein the plurality of sensor devices includes a time-of-flight distance sensor paired with an imaging sensor, wherein the time-of-flight distance sensor is adapted to contribute object size information to image information captured by the imaging sensor.

12) The monitoring system of any of solutions 1-11, wherein the plurality of sensor devices includes at least three of the following types of sensor devices: a temperature sensor, an ambient light sensor, a humidity sensor, a barometer sensor, an air quality sensor, an infrared sensor, a carbon dioxide sensor, a carbon monoxide sensor, a piezoelectric sensor, or an airflow sensor.

13) The monitoring system of any of solutions 1-12, wherein the activity information includes both environmental information for the area and information regarding one or more individuals that are present within the area.

14) The monitoring system of solution 13, wherein the environmental information includes one of temperature, humidity, sounds, or airflow, and the information regarding the one or more individuals includes a medical condition or an amount of daily activity.

15) A monitoring system, comprising: one or more sensor devices each configured to collect sensor data from a respective environment, wherein the one or more sensor devices are positioned within a structure; and a hub device positioned within the structure. The hub device is configured to dynamically include a new sensor device with the one or more sensor devices; obtain sensor data that originates from the one or more sensor devices; generate a heatmap of one or more areas within the structure based on classifying activity information captured by the sensor data, wherein the heatmap identifies types of activities, locations of activities, and the sensor devices involved in detecting activities; use the heatmap as a reference to determine whether an occurrence or non-occurrence of a particular activity deviates from the heatmap activities; and in response to determining that a deviation has occurred, generate a notification indicative of the deviation.

16) The monitoring system of solution 15, wherein the one or more sensor devices are included within the hub device.

17) A hub device of a monitoring system that includes a plurality of sensor devices distributed across an area, the hub device including a processor and a memory having instructions stored therein, wherein instructions upon execution by the processor configure the processor to: dynamically maintain a network whitelist that identifies the plurality of sensor devices; receive, from one or more satellite devices, sensor data originating from the plurality of sensor devices; generate an activity record of the area based on classifying activity information captured by the sensor data; and in response to determining that an occurrence or non-occurrence of a particular activity deviates from the activity record in a particular sensor data, transmit an alert notification to a user device.

18) The hub device of solution 17, wherein dynamically maintaining the network whitelist comprises: detecting a broadcasted signal on an open receive channel, the broadcasted signal originating from a new sensor device not identified by the network whitelist; performing a series of network performance tests with the new sensor device; and update the network whitelist to additionally identify the new sensor device.

19) The hub device of any of solution 17 or solution 18, wherein the plurality of sensor devices includes a pendant device carried by an individual and configured for cellular network communication.

20) The hub device of any of solutions 17-19, wherein the activity record is specific to an individual, and wherein the user device to which the alert notification is transmitted is associated with a caregiver responsible for the individual and located remote to the area.

21) The hub device of any of solutions 17-20, wherein the hub device comprises: a wireless controller via which the hub device communicates with the one or more satellite devices; a microcontroller unit that includes the processor; and a microelectromechanical inertial measurement unit (IMU) coupled to the microcontroller unit, wherein the microelectromechanical IMU is configured to change a state of the microcontroller unit to a powered-on state in response to a movement effected on the microelectromechanical IMU.

22) The hub device of any of solutions 17-21, wherein the activity record is generated in the memory of the hub device, the memory for the activity record being partitioned into rows and columns, wherein each row of the memory for the activity record corresponds to a different sensor device from which the sensor data originates, and wherein each column of the memory for the activity record corresponds to a different time period in which the hub device receives sensor data originating from the plurality of sensor devices.

A remote computing device may be a smart device, a smart phone, a vehicle, a tablet, a laptop, a TV, or any electronic device capable of wirelessly connecting to a network or joining a wireless network. The remote computing device may be wirelessly and communicably associated to an individual either through a network or server (e.g., through a user account on the server, or WiFi™ login information), or through visual information collected by the hub device. The terms remote computing device, individual, and user may be used interchangeably throughout the present disclosure.

The server may be a computer that provides data to other computers. It may serve data to systems on a local area network (LAN) or a wide area network (WAN) over the Internet. The server may comprise of one or more types of servers (e.g., a web server or file server), each running its own software specific to the purpose of the server for sharing services, data, or files over a network. The server may be any computer configured to act as a server (e.g., a desktop computer, or single or multiple rack-mountable servers) and accessible remotely using remote access software.

Proximity determination may be made by using a combination of visual, motion, and audio information. The sensor components or sensors, server, remote computing device, and/or monitoring system (hub device, satellite device, and/or sensor device) may define a virtual perimeter for a real-world geographic area. The monitoring system may also respond to geofencing triggers. Geofencing may be accomplished using location aware devices through, for example, GPS, RFID technology, wireless network connection information, cellular network connection information, etc. Visual, motion, and audio information may be collected by the monitoring system or server to substantiate an individual(s)/remote computing device(s) physical location.

The network may be a network of computers, a local area network (LAN), a wide area network (WAN), or an Intranet, or a network of networks, for example, the Internet. Moreover, various interfaces may be used to connect to the network such as cellular interfaces, WiFi™ interfaces. Infrared interfaces, RFID interfaces, ZigBee interfaces, Bluetooth interfaces, Ethernet interfaces, coaxial interfaces, optical interfaces, or generally any communication interface that may be used for device communication. The purpose of the network is to enable the sharing of files and information between multiple systems.

Low Power Wi-Fi Device Example

A popular trend today in microcontroller design is the incorporation of more analog circuitry into the microcontroller alongside the digital transistor circuitry delivering a sub-category of microcontroller unit (MCU) called a system-on-a-chip (SOC). A capability found in many common SOC integrated ICs is the integration of a 2.4 GHz radio that can be programmed to transmit or receive data. Unfortunately, these ICs are very difficult to use in battery-operated devices when they are designed for using the Wi-Fi protocol because of their high current requirements. Even in their lowest-powered operating modes of 'Sleep Mode' or 'Idle Mode', these MCUs consume too much power to allow a battery powered device to operate for long periods of time. A separate trend in IC development today is found in microelectromechanical systems (MEMS) ICs. Today, several MEMS inertial measurement devices (IMUs) integrate digital transistor logic circuitry that can be used to analyze analog inertial measurements without assistance from the MCU. Certain aspects of the disclosed technology can be implemented in embodiments that use extremely low-power operating mode of the IMUs internal logic circuitry to act as a power-on watchdog that bootstraps the MCU when necessary. The MCU may be completely powered off; for instance, an ESP8266 from Espressif may be completely powered off by, for example, pulling down the chip enable pin to ground to completely power off the chip. Quiescent power to the IMU may be kept on which would now have its processing clock set to the lowest rate (~25 Hz). When there is a jerk—an acceleration of acceleration—an interrupt may be generated from the IMU, and the chip enable pin on the MCU may be set high to allow it to power on. After running its instructions, the MCU powers itself down again until the next time the IMU awakens it. This process, among others disclosed in the present disclosure, may be used to greatly extend battery life of the device.

Example Latch to Determine State

A challenge with using hardware to monitor the environment without actively powered logic control is dealing with the lack of continuous state information. In some embodiments of the disclosed technology, components of the monitoring system incorporate a button (capacitive, touchscreen, mechanical, or the like) that allows a user to press to wake any component device of the monitoring system. Any or all components of the monitoring system may include an IMU to detect environmental motion to wake the component device. However, this presents a problem to solve when there is no active MCU. When a user presses a button on the device, this suddenly causes motion. The challenge is to differentiate the action that triggered the MCU to power-on:

was it simply detected motion? Or was it motion caused by a button being pressed? According to an embodiment, by implementing a resettable latch that is set by the button being pressed that can be recognized by the MCU once powered-on and can then be reset or unset by the MCU before powering back down. For example, using an ESP8285 as our MCU, and an IMU similar to the Bosch BMA400 or the ST LIS2DW12, a latch using a simple JK flip-flop may be set, that is, set by the button being pressed, read by the MCU upon powering up, and then reset before powering back down. This process, among others disclosed in the present disclosure, may be used to greatly reduce the cost of materials required to implement a stateful response.

Predefined Conference Bridge Example

Modern commercial or home monitoring or commercial and home security devices are typically designed to allow an individual user to see and respond to events which occur in the building or home. Some of these devices are designed to allow for multiple users to simultaneously see events, but in all cases, during the response period, there is a single user in control. When dealing with a group of peers monitoring and responding simultaneously it is often problematic dealing with voice communication between the peers. One of the features of the disclosed technology includes use of full-duplex VOIP telephony capability incorporated into at least the hub device of the monitoring system. The hub device is typically installed in the facility being monitored. During the user setup process, a virtual conference bridge on a cloud-based PBX is created that is unique to the hub device and shared within the group of peers. According to an example embodiment, when users enroll to become part of the peer group that will be monitoring the home or building which this hub device has been installed, the connection address and encryption keys and certificates are shared with the new user joining the group. All peered users running an application on their mobile phone, and all of the devices incorporating our VOIP technology installed in the home, are able to send and receive command signals sent over standard IP protocol signaling when to join the preestablished conference bridge. In one example embodiment, an ESP32 MCU from Espressif and a ZLS38063 DSP from Micro Semi, or the like, may be incorporated into the hub device to implement hands-free full-duplex telephony using the hub device. The ESP32 connects to the public network using a Wi-Fi connection and makes a secure and encrypted connection to a message broker running on a remote server. This message broker connects all peers remotely monitoring the hub device. When any remote peer wishes to establish a voice call to the hub device or with other users in the peer group, they send a signal via this message broker signaling the recipients to connect to the already established conference bridge. MQTT may be used, for example, on the hub device as the message transport and AWS IoT MQTT as our message broker. The connection may be implemented securely as, for example, a Transport Layer Security (TLS) encrypted IP connection.

This solves many problems, a few of which include:
1. None of the participants in the call need to dial in to a dynamically changing number.
2. All of the participants can opt-in or opt-out of a call.
3. The participants can be automatically connected (hands-free).
4. It results in dramatically lowered costs and simplified scaling, balancing, privacy capabilities, and security capabilities by removing dynamic circuit switching requirements, and handling conference calls in an atomic and discreet manner that allows conference groups to be distributed across multiple independent servers.

Localized Device Provisioning Examples

Devices designed to automate tasks in the home sold today suffer from a requirement that they be individually provisioned by the user to connect to the local wireless network in the home. Devices which are made using common 2.4 GHz wi-fi radio technology, must have their security credentials including the id of their local wireless access point and the access password, shared individually one at a time with each new device being added into the home. Additionally, these devices typically join the wireless network in a haphazard and unbalanced manner creating network bottlenecks and often result in poor network performance for all devices connected to that local wireless network.

The component devices in the monitoring system according to the disclosed technology can solve this problem and others by using out-of-band radio signaling between new devices to securely share credentials with minimal user intervention and providing for deterministic load-balancing of the devices connected onto the wireless network. For example, several modern SOC ICs incorporating 2.4 GHz radios can support a connection-less transport mode that allows UDP formatted packets to be sent over short distances to devices without an established Wi-Fi connection. In this manner, a central controller (e.g., a hub device, or a satellite device) may be established similar to a domain name server (DNS) on the first device that a customer installs and connects to their home wireless network. In one exemplary method, during this installation, the customer inputs the network security credentials through a cryptographically secure wireless connection with an app running on their mobile phone. Then, when new devices are powered on within the premises, a signal is broadcast from the new device on a generic address that is always available as an open receive channel. The central controller monitors this open receive channel and when a new device is detected wirelessly transmitting on this channel, makes a request through the secure connection to the mobile phone requesting acknowledgment and permission to connect this new device. If the permission is granted, the central controller performs a series of tests with the new device by sending wireless signals back and forth to determine wireless network quality characteristics and makes a determination using a smart algorithm comparing packet loss, signal strength, and other parameters to implement the best solution to balance the wireless network load with all of the other devices in the network. Then the credentials are transmitted by the central controller to the new device so that the new device can establish and maintain a secure connection to the network.

Examples of Connectionless Devices and Connected Devices

A common way to operate a wireless radio for data transmission at low power is to reduce the number of transmissions required to establish a connection 'channel' between devices. Typically, before a device can transmit data, a series of small signals are sent between the device and a host device on a number of different sub-frequencies and signal tests are performed to establish and optimal sub-frequency to use to send data. This ideal sub-frequency for the transmission is called the 'channel'. The current wireless technology common in homes is 2.4 GHz or 5 GHz Wi-Fi. Radio transmissions using 2.4 GHz frequency require much lower power than radio transmissions using higher 5 GHz frequency communication. However, radio signals sent on the 2.4 GHz frequency have far fewer subchannels available than does 5 GHz. One way to reduce the power of devices using wireless radio technology is to cache the channel connection information to reduce the number of transmissions needed to establish the ideal channel to use and also to reduce the number of devices which require two-way transceiver capability from devices which may only require one-way transmit or receive capability.

According to some embodiments of the disclosed technology, the component devices in the monitoring system can address this issue by using two classes of devices: those that have radio transceivers that have larger power supply; and those that have only radio transmitters that have less supplied power. The component devices classified as such in a network topology may be further optimized to form a balanced network topology where the lower powered devices are connected to nodes in the network in an Extended Star topology. The component devices of the monitoring system of the present disclosure may dynamically assign the low power transmit-only devices to be connected to local transceiver equipped devices which act as host nodes and have much greater available power. The connection between the low-powered devices and the high-powered devices is cached and when it is necessary to transmit data, the sender is relieved from the unnecessary steps of establishing the connection channel. The data is sent with the least required amount of power. The component devices in the monitoring system of the present disclosure may be distributed as multiple nodes through the area where each component device has access to high power and transceiver radio capability and where each of many component devices may establish a dynamic connection of low power communicating with these nodes in a balanced network configuration. In some embodiments, some of the component devices in the monitoring system of the present disclosure may be low-powered transmit-only devices that utilize SOCs like the ESP8266. While component devices in the monitoring system of the present disclosure having higher-powered transceiver equipped devices may incorporate both an ESP32 connected to a local Wi-Fi network and an ESP8266 in a receive-only state to communicate with the low-powered devices. This allows the high-powered nodes to dynamically adjust their network connections using the capabilities of the Wi-Fi protocol to maximize throughput and maintain robust connection, while also allowing us to maintain low-power connections using a cached channel RF protocol.

PIR CPLD Example

Passive Infrared motion sensors (PIR sensor) typically operate in a binary fashion—setting an electrical signal high to indicate detection of a warm body in nearby motion or low to indicate a lack of detected motion. To dampen the generation of excess signals sent from these devices, there is typically a timed latch capability so that the circuit can clamp a high signal for a fixed amount of time before releasing the clamp and resetting the circuit to detect motion again. Some PIR sensors incorporate logic ICs so that to allow the time value used for the clamp circuit to be adjusted by control logic running on a host microcontroller or to adjust the setpoint temperature used to determine if a warm body in motion is detected. In both of these PIR circuits, the amount of information that is available to the host microcontroller is too limited to detect a wide range of parameters that may be useful to the application. In some embodiments, the component devices in the monitoring system of the present disclosure may integrate a low-cost PIR sensor with a complex programmable logic device (CPLD) along with a time-of-flight distance sensor to allow a large range of parameters to be detected deterministically while maintaining a very low cost and very few number of components. A PIR sensor connected to a CPLD IC can be programmed to allow a complex waveform to be recorded that is broken into fixed time intervals. Incorporating a time-of-flight distance sensor provides the added fidelity required to detect complex motion activities using inexpensive components. The component devices in the monitoring system of the present disclosure can detect with high fidelity the relative size of the object in motion, the direction and rate of travel, and detect when the sensor is blocked by an inanimate object. The parameters extracted from this circuit are robust enough to be input into a stochastic table generated by a machine learning process (probabilistic signal determination) or run through a rule-based process (deterministic signal determination).

Example Array of PID Functions to Determine ADLs

A challenge in the field of monitoring the activities of the elderly living alone is determining their activities of daily life (ADLs). For instance: bathing, eating, sleeping, exercise. Current solutions involve incorporation of multiple cameras viewing the older person and streaming the video to a remote server where visual analysis is performed, or by integrating complex and expensive sensors in the home environment to measure and record activities. In some embodiments of the disclosed technology, the monitoring system may use a mechanism to deterministically recognize activities using common low-cost sensors, where the fidelity of signal can easily be increased simply with the addition of more low-cost sensors. The component devices in such a monitoring system can provide deterministic solution rather than only probabilistic.

In an example embodiment, the monitoring system may incorporate a microcontroller operating as a master control device. The component devices may be wirelessly connected to an arbitrary number of smaller wireless devices each containing a minimum of one sensor. The output of each sensor is reported from the smaller devices to the master control device for analysis. The master control device (e.g., hub device) incorporates memory storage that is partitioned into rows and columns. Each sensor output is recorded into one cell in the memory based on the time it occurred. Arbitrarily we can choose each row to represent a different sensor, and each column to represent a different hour within a 30-day period. Each sensor in this platform is configured with a threshold value. When a sensor input exceeds the threshold value, a signal is sent from the device to the master control device with the magnitude of the detected signal. The master control device runs a filtering algorithm on the received sensor data (a PID function works well but it could be various different algorithms) and then stores the filtered data in its partitioned memory based on the sensor id and the current time.

The partitioned memory then represents a heat-map of sorts, which can show the time and sensor readings that are expected to be generated at any given moment. Accordingly, ADLs can be deterministically measured and deviations for regular activities be detected—either activities occurring when none usually occur, or activities not occurring when they usually do occur.

Example Hierarchical Organization of Inexpensive Simple Sensors to Adjudicate Triggers on Complex Behaviors In some embodiments of the present technology, by hierarchically attaching sensors based on their location information, the master control device (e.g., the hub device) is able to adjudicate the generation of triggers based on complex behaviors that would not be discernable by any individual sensor. Additionally, the fidelity of the adjudication of these triggers can be increased at any time by the addition of additional inexpensive sensors.

Image Sensor Incorporating a Time-Of-Flight Distance Sensor to Approximate Z for Object Classification.

Passive infrared motion detection is very popular due to its low cost. More complex motion detection is possible using imaging sensors; however, their increased cost is usually not justified over the low-cost passive infrared unless the application requires video to be recorded or to be streamed remotely. The capabilities of the low cost PIR are usually good enough for local processing of motion detection, and the added capabilities of the image sensor are not utilized unless the device is recording video.

In some embodiments of the present technology, by incorporating a time-of-flight distance sensor it is possible to create a much more robust motion detection circuit that can be useful for local processing even when video recording is not being utilized. A standard image sensor captures light arriving onto a sensor through a view frustum. The data captured from the sensor can be processed by a microcontroller to determine an object in motion and determine the extents of the pixels that had changed; this methodology produces results that are not too dissimilar to what a PIR can detect although much more expensively. By incorporating a time-of-flight distance sensor along with an imaging sensor, we can make a good estimation of the objects size. Combined with the other data, we can detect the size, volume, speed of travel, orientation, and make a count of the number of independent objects in motion within the view frustum. The image sensor (e.g., hub device) and passive infrared sensor (e.g., satellite device) may be used interchangeably, for example, to obtain X- and Y-components of motion within a space. The extracted X- and Y-component information may then be combined with the time-of-flight sensor to obtain Z-component to obtain a good estimation of object size and motion in a space, a process similar to Light Detection and Ranging (LIDAR).

Moreover, in some embodiments, various camera types may be used (e.g., near-infrared light source and a single photosensor) to detect the progression of microvascular damage that precedes the development of a decubitus ulcer. In some embodiments, a macro camera may be implemented in one of the sensor components (e.g., sensor device or cellular pendant) to give patients or caregivers the ability to immediately photograph and communicate skin or other visually apparent developing conditions to a healthcare provider (e.g., through an HMI interface of a mobile device) to determine proper medication or activity for treatment or care. Moreover, the hub device and sensor components may be configured to monitor for certain related activity for treatment or care or to notify the care giver (user) for proper over the counter medication or purchasing of comfort care items.

Example Classifier on Video and/or Audio (Edge Computing)

One of the challenges of running audio or video ML classifiers on embedded microcontrollers rather than processing the information on remote servers where they are receiving the audio and video data via streams is the lack of computation power on the microcontroller versus the computation power on the remote servers. One improvement to this problem is to allow the ML classifiers to perform earlier trivial rejection of data and reduce the required processing to run the audio and video classifiers.

The classifiers of the present disclosure may be binary state machines which are compiled on computers with large processing capability and access to large amounts of memory that analyze large diverse datasets to reduce the state machines down to the minimum size possible to detect one of the datasets. These binary classifiers are then installed onto microcontrollers with limited processing capabilities and access to much less memory.

A problem arises when the initial dataset is very diverse. The more diverse the original dataset then the larger the compiled classifier will be. One possible optimization of this process is to dynamically exchanges the binary classifiers that are running on a device to match only the datasets that are represented in that environment.

In some embodiments, the component devices in the monitoring system of the present disclosure may solve this issue and others by installing classifiers on devices that are generic and large when they are first attached to a wireless network. Using other sources of audio and video that are captured using the customers mobile device, optimized classifiers can be selected and installed onto the wireless device using an over-the-air (OTA) update to the microcontroller's firmware.

In various embodiments of the present disclosure, the component devices may include numerous inexpensive commodity hardware that may be used to facilitate comprehensive space and environmental information collection. Instead of providing probable outcomes or analyzing behavior using learning algorithms, artificial intelligence and/or machine learning, such inexpensive commodity hardware may be distributed throughout a building to consistently monitor one or more aspects of individual or patient activity thereby providing deterministic analysis. Thus, the care giver (user) experience is improved as the care giver (user) has peace of mind knowing events and activity that support the well-being of a patient have occurred. Also, the care giver (user) experience is improved as the care giver (user) has the information necessary (e.g., amount of walking during the day as determined by a component sensor) for planning daily changes in patient activity to improve the well-being of the monitored patient.

The following lists certain examples of embodiments disclosed herein.

1) A monitoring device, comprising: at least one memory; at least one button; one or more light emitting sources; and a processor, the processor coupled to the at least one memory and communicably coupled to at least one inertial measurement unit; wherein the processor is configured to adjust the operating mode of the monitoring device based on a state of the at least one inertial measurement unit; wherein the processor is communicably coupled to one or more sensors and configured to classify one or more activities communicated from the one or more sensors.

2) The monitoring device of example 1, wherein one of the one or more sensors includes a time-of-flight sensor.

3) The monitoring device of any of examples 1 or 2, wherein when the at least one inertial measurement unit receives a first input, the state of the at least one inertial measurement unit goes into a first state and an operating mode of the monitoring device is set to a low power operating mode.

4) The monitoring device of example 3, wherein pressing the at least one button communicates the first input to the inertial measurement unit.

5) The monitoring device of any of examples 1-4, wherein the processor is configured to adjust the operating mode of the monitoring device based on one or more activities communicated from the one or more sensors.

6) The monitoring device of any of examples 1-5, wherein one of the one or more sensors includes a microphone communicable coupled to the processor, and wherein the processor is further configured to initiate a voice of internet protocol (VOIP) session upon detecting an audio signature from the microphone.

7) The monitoring device of any of examples 1-6, wherein the processor is configured to classify an activity based on the activity being communicated as occurring in a plurality of the one or more sensors.

8) A monitoring system implemented as described in this patent document.

9) A method for monitoring a building or enclosure according to any of the methodologies described in this patent document.

Those of skill in the art will appreciate that some of the foregoing disclosed systems and functionalities may be designed and configured into computer files (e.g., RTL, GDSII, GERBER, etc.) stored on computer-readable media. Some or all such files may be provided to fabrication handlers who fabricate devices based on such files. Resulting products include semiconductor wafers that are separated into semiconductor dies and packaged into semiconductor chips. The semiconductor chips are then employed in devices, such as, an IoT device, a monitoring system, or any combination thereof.

Those of skill would further appreciate that the various illustrative logical blocks, configurations, modules, circuits, and algorithm steps described in connection with the embodiments disclosed herein may be implemented as electronic hardware, computer software executed by a processor, or combinations of both. Various illustrative components, blocks, configurations, modules, circuits, and steps have been described above generally in terms of their functionality. Whether such functionality is implemented as hardware or processor executable instructions depends upon the particular application and design constraints imposed on the overall system. Skilled artisans may implement the described functionality in varying ways for each particular application, but such implementation decisions should not be interpreted as causing a departure from the scope of the present disclosure.

The steps of a method or algorithm described in connection with the embodiments disclosed herein may be embodied directly in hardware, in a software module executed by a processor, or in a combination of the two. A software module may reside in random access memory (RAM), flash memory, read-only memory (ROM), programmable read-only memory (PROM), erasable programmable read-only memory (EPROM), electrically erasable programmable read-only memory (EEPROM), registers, hard disk, a removable disk, a compact disc read-only memory (CD-ROM), or any other form of non-transient storage medium known in the art. An exemplary storage medium is coupled to the processor such that the processor may read information from, and write information to, the storage medium. In the alternative, the storage medium may be integral to the processor. The processor and the storage medium may reside in an application-specific integrated circuit (ASIC). The ASIC may reside in a computing device or a user terminal. In the alternative, the processor, and the storage medium may reside as discrete components in a computing device or user terminal.

Further, specific details are given in the description to provide a thorough understanding of the embodiments. However, embodiments may be practiced without these specific details. For example, well-known circuits, processes, algorithms, structures, and techniques have been shown without unnecessary detail to avoid obscuring the embodiments. This description provides example embodiments only and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

Where applicable, various embodiments provided by the present disclosure may be implemented using hardware, software, or combinations of hardware and software. In addition, where applicable, the various hardware components and/or software components, set forth herein, may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

Software or application, in accordance with the present disclosure, such as program code and/or data, may be stored on one or more computer-readable mediums. It is also contemplated that software identified herein may be implemented using one or more general purpose or specific purpose computers and/or computer systems, networked and/or otherwise. Where applicable, the ordering of various steps described herein may be changed, combined into composite steps, and/or separated into sub-steps to provide features described herein.

It should be noted that the methods described above describe possible implementations, and that the operations and the steps may be rearranged or otherwise modified and that other implementations are possible. Furthermore, embodiments from two or more of the methods may be combined.

From the foregoing, it will be appreciated that specific embodiments of the present disclosure have been described herein for purposes of illustration, but that various modifications may be made without deviating from the scope of the present disclosure. Rather, in the foregoing description, numerous specific details are discussed to provide a thorough and enabling description for embodiments of the present disclosure. One skilled in the relevant art, however, will recognize that the disclosure can be practiced without one or more of the specific details. In other instances, well-known structures or operations often associated with memory systems and devices are not shown, or are not described in detail, to avoid obscuring other aspects of the present disclosure. In general, it should be understood that various other devices, systems, and methods in addition to those specific embodiments disclosed herein may be within the scope of the present disclosure.

The invention claimed is:

1. A monitoring system, comprising:
a plurality of sensor devices each configured to collect sensor data from a respective environment, wherein the plurality of sensor devices are spread across multiple locations within an area;
one or more satellite devices each configured to facilitate wireless communication between the plurality of sensor devices and a hub device of the monitoring system; and
the hub device configured to communicate with the one or more satellite devices, wherein the hub device is further configured to:
dynamically add a new sensor device to the plurality of sensor devices in response to the new sensor device broadcasting a signal on an open receive channel monitored by the hub device and further in response to receiving an acknowledgment to a query transmitted by the hub device to a user device, the query identifying the new sensor device;
receive, from the one or more satellite devices, sensor data that originates from the plurality of sensor devices;
generate an activity record of the area based on classifying activity information captured by the sensor data; and
in response to determining that an occurrence or non-occurrence of a particular activity deviates from the activity record in a particular sensor data, transmit an alert notification to the user device.

2. The monitoring system of claim 1, wherein the one or more satellite devices are each configured to communicate with the plurality of sensor devices via a first communication protocol, and communicate with the hub device via a second communication protocol.

3. The monitoring system of claim 1, wherein dynamically adding the new sensor device to the plurality of sensor devices includes building a whitelist that identifies each of the plurality of sensor devices.

4. The monitoring system of claim 1, wherein the activity record comprises a heatmap that identifies locations and frequencies of activity occurrences.

5. The monitoring system of claim 1, wherein the plurality of sensor devices includes a pendant device carried by an individual and configured for cellular network communication.

6. The monitoring system of claim 1, wherein the activity record is specific to an individual being monitored by the monitoring system, and wherein the user device to which the alert notification is transmitted is associated with a caregiver responsible for the individual and located remote to the area.

7. The monitoring system of claim 1, wherein the plurality of sensor devices includes a particular sensor device comprising:
a wireless controller via which the particular sensor device communicates with the one or more satellite devices;
a microcontroller unit configured to execute instructions to operate the wireless controller; and
a microelectromechanical inertial measurement unit (IMU) coupled to the microcontroller unit, wherein the microelectromechanical IMU is configured to provide a digital input to the microcontroller unit to change a state of the microcontroller unit to a powered-on state in response to a movement effected on the microelectromechanical IMU.

8. The monitoring system of claim 7, wherein the microelectromechanical IMU is coupled to a chip enable pin of the microcontroller unit that is configured to maintain the microcontroller unit in a powered-off state until the microelectromechanical IMU provides the digital input to change the state of the microcontroller units.

9. The monitoring system of claim 1, wherein the hub device is configured to generate the activity record in a memory storage that is partitioned into rows and columns, wherein each row of the memory storage corresponds to a different sensor device from which the hub device receives sensor data, and wherein each column of the memory storage corresponds to a different time period in which the hub device receives sensor data from the plurality of sensor devices.

10. The monitoring system of claim 1, wherein the plurality of sensor devices includes a time-of-flight distance sensor paired with an imaging sensor, wherein the time-of-flight distance sensor is adapted to contribute object size information to image information captured by the imaging sensor.

11. The monitoring system of claim 1, wherein the plurality of sensor devices includes at least three of the following types of sensor devices: a temperature sensor, an ambient light sensor, a humidity sensor, a barometer sensor, an air quality sensor, an infrared sensor, a carbon dioxide sensor, a carbon monoxide sensor, a piezoelectric sensor, or an airflow sensor.

12. The monitoring system of claim 1, wherein the activity information includes both environmental information for the area and information regarding one or more individuals that are present within the area.

13. The monitoring system of claim 12, wherein the environmental information includes one of temperature, humidity, sounds, or airflow, and the information regarding the one or more individuals includes a medical condition or an amount of daily activity.

14. A monitoring system, comprising:
one or more sensor devices each configured to collect sensor data from a respective environment, wherein the one or more sensor devices are positioned within a structure; and
a hub device positioned within the structure and configured to:
dynamically include a new sensor device with the one or more sensor devices in response to the new sensor device broadcasting a signal on an open receive channel monitored by the hub device and further in response to receiving an acknowledgment to a query transmitted by the hub device to a user device, the query identifying the new sensor device;
obtain sensor data that originates from the one or more sensor devices;
generate a heatmap of one or more areas within the structure based on classifying activity information captured by the sensor data, wherein the heatmap identifies types of activities, locations of activities, and the sensor devices involved in detecting activities;

use the heatmap as a reference to determine whether an occurrence or non-occurrence of a particular activity deviates from the heatmap activities; and in response to determining that a deviation has occurred, generate a notification indicative of the deviation.

15. The monitoring system of claim 14, wherein the one or more sensor devices are included within the hub device.

16. A hub device of a monitoring system that includes a plurality of sensor devices distributed across an area, the hub device including a processor and a memory having instructions stored therein, wherein instructions upon execution by the processor configure the processor to:

dynamically maintain a network whitelist that identifies the plurality of sensor devices, wherein dynamically maintaining the network whitelist comprises:

detecting a broadcasted signal on an open receive channel, the broadcasted signal originating from a new sensor device not identified by the network whitelist;

performing a series of network performance tests with the new sensor device; and update the network whitelist to additionally identify the new sensor device;

receive, from one or more satellite devices, sensor data originating from the plurality of sensor devices;

generate an activity record of the area based on classifying activity information captured by the sensor data; and in response to determining that an occurrence or non-occurrence of a particular activity deviates from the activity record in a particular sensor data, transmit an alert notification to a user device.

17. The hub device of claim 16, wherein the plurality of sensor devices includes a pendant device carried by an individual and configured for cellular network communication.

18. The hub device of claim 16, wherein the activity record is specific to an individual, and wherein the user device to which the alert notification is transmitted is associated with a caregiver responsible for the individual and located remote to the area.

19. The hub device of claim 16, wherein the hub device comprises:

a wireless controller via which the hub device communicates with the one or more satellite devices;

a microcontroller unit that includes the processor; and a microelectromechanical inertial measurement unit (IMU) coupled to the microcontroller unit, wherein the microelectromechanical IMU is configured to change a state of the microcontroller unit to a powered-on state in response to a movement effected on the microelectromechanical IMU.

20. The hub device of claim 16, wherein the activity record is generated in the memory of the hub device, the memory for the activity record being partitioned into rows and columns, wherein each row of the memory for the activity record corresponds to a different sensor device from which the sensor data originates, and wherein each column of the memory for the activity record corresponds to a different time period in which the hub device receives sensor data originating from the plurality of sensor devices.

21. A method for a monitoring system for an area, the method comprising:

collecting, by a processor via a plurality of sensor devices of the monitoring system that are distributed across the area, activity information of an individual within the area;

classifying, by the processor, the activity information based on comparing the activity information with historical activity information stored in a database;

generating, by the processor, an activity heatmap based on updating a number of activity occurrences according to the classified activity information;

in response to detecting a non-occurrence of a normally-occurring activity identified by the activity heatmap, providing, by the processor, an alert notification to a user device associated with the individual; and providing, by the processor, placement information that indicates where to place the plurality of sensor devices within the area based on the activity heatmap.

22. The method of claim 21, wherein collecting the activity information comprises:

capturing, by the plurality of sensor devices, sensor data that includes the activity information of the individual within the area;

receiving, by a satellite device of the monitoring system, sensor data that includes the activity information from the plurality of sensor devices; and providing, by the satellite device, the activity information to the processor.

23. The method of claim 21, wherein the activity heatmap generated in a memory storage that is partitioned into rows and columns, wherein each row of the memory storage corresponds to a different sensor device from which the activity information originates, and wherein each column of the memory storage corresponds to a different time period with which the activity information is associated.

24. The method of claim 21, further comprising:

dynamically including a new sensor device with the plurality of sensor devices based on in response to the new sensor device broadcasting a signal on a monitored open receive channel; and collecting activity information of the individual from the new sensor device.

25. The method of claim 21, wherein the activity information includes at least one of a temperature, humidity, sounds, or airflow of the area and individual information that includes a medical condition or an amount of daily activity of the individual.

26. The method of claim 21, wherein detecting the non-occurrence of the normally-occurring activity is performed using a deterministic analysis based on the activity heatmap and detections obtained from one or more of the plurality of sensor devices.

27. A monitoring system, comprising:

a plurality of sensor devices each configured to collect sensor data from a respective environment, wherein the plurality of sensor devices are spread across multiple locations within an area;

one or more satellite devices each configured to facilitate wireless communication between the plurality of sensor devices and a hub device of the monitoring system; and the hub device configured to communicate with the one or more satellite devices, wherein the hub device is further configured to:

dynamically add a new sensor device to the plurality of sensor devices, wherein the plurality of sensor devices includes a time-of-flight distance sensor paired with an imaging sensor, wherein the time-offlight distance sensor is adapted to contribute object size information to image information captured by the imaging sensor;

receive, from the one or more satellite devices, sensor data that originates from the plurality of sensor devices;

generate an activity record of the area based on classifying activity information captured by the sensor data; and in response to determining that an occurrence or non-occurrence of a particular activity deviates from the activity record in a particular sensor data, transmit an alert notification to a user device.

28. A hub device of a monitoring system that includes a plurality of sensor devices distributed across an area, the hub device including a processor and a memory having instructions stored therein, wherein instructions upon execution by the processor configure the processor to:

dynamically maintain a network whitelist that identifies the plurality of sensor devices;

receive, from one or more satellite devices, sensor data originating from the plurality of sensor devices;

generate an activity record of the area based on classifying activity information captured by the sensor data, wherein the activity record is generated in the memory of the hub device, the memory for the activity record being partitioned into rows and columns, wherein each row of the memory for the activity record corresponds to a different sensor device from which the sensor data originates, and wherein each column of the memory for the activity record corresponds to a different time period in which the hub device receives sensor data originating from the plurality of sensor devices; and in response to determining that an occurrence or non-occurrence of a particular activity deviates from the activity record in a particular sensor data, transmit an alert notification to a user device.

* * * * *